(12) United States Patent
Sutcliffe et al.

(10) Patent No.: US 8,714,853 B2
(45) Date of Patent: May 6, 2014

(54) DISPENSER

(75) Inventors: Adam F. R. Sutcliffe, Middlesex (GB); Robin B. K. Chilton, London (GB); Graeme H. Davies, London (GB); Katie L. Goodwin, London (GB)

(73) Assignee: Orbel Health Limited, London (GB)

( * ) Notice: Subject to any disclaimer, the term of this patent is extended or adjusted under 35 U.S.C. 154(b) by 897 days.

(21) Appl. No.: 12/308,381

(22) PCT Filed: Jun. 14, 2007

(86) PCT No.: PCT/GB2007/002225
§ 371 (c)(1),
(2), (4) Date: Dec. 12, 2008

(87) PCT Pub. No.: WO2007/144634
PCT Pub. Date: Dec. 21, 2007

(65) Prior Publication Data
US 2010/0054847 A1    Mar. 4, 2010

(30) Foreign Application Priority Data
Jun. 14, 2006 (GB) .................................. 0611809.5

(51) Int. Cl.
*A46B 11/00* (2006.01)
(52) U.S. Cl.
USPC .......................................................... 401/28
(58) Field of Classification Search
USPC ....................................................... 401/28, 16
See application file for complete search history.

(56) References Cited

U.S. PATENT DOCUMENTS

| 2,285,105 | A | * | 6/1942 | Bacher | 601/113 |
| 3,961,852 | A | * | 6/1976 | Parry | 401/195 |
| 4,037,977 | A | * | 7/1977 | Ronai | 401/209 |
| 4,492,223 | A | * | 1/1985 | Burke | 601/154 |
| 5,851,077 | A |  | 12/1998 | Trego | |
| 5,938,363 | A | * | 8/1999 | Timms et al. | 401/209 |
| 6,729,787 | B2 |  | 5/2004 | Usami et al. | |
| 6,821,043 | B2 | * | 11/2004 | Teh | 401/39 |
| 6,877,642 | B1 | * | 4/2005 | Maddox et al. | 222/181.3 |
| 6,925,672 | B1 |  | 8/2005 | Bromley | |
| 6,983,864 | B1 |  | 1/2006 | Cagle | |
| 7,988,020 | B2 |  | 8/2011 | Shoham et al. | |

FOREIGN PATENT DOCUMENTS

| DE | 4219310 | 12/1992 |
| DE | 202004018315 | 4/2005 |
| DE | 202005012664 | 2/2006 |
| EP | 0375579 | 6/1990 |
| EP | 1277595 A1 | 1/2003 |
| FR | 2356571 | 1/1978 |
| GB | 2215673 | 9/1989 |

(Continued)

OTHER PUBLICATIONS

English Abstract of DE 4219310, Dec. 1992.

(Continued)

*Primary Examiner* — Huyen Le
(74) *Attorney, Agent, or Firm* — Levenfeld Pearlstein, LLC

(57) ABSTRACT

The present invention relates to a dispenser for a hand treatment product. The dispenser (1) comprises an applicator (3), a hand treatment product storage reservoir (5) in fluid communication with the applicator (3), and a restraining means (7) for restraining the dispenser to a support surface, wherein, in use, when a hand is moved across the applicator (3), hand treatment product is applied to the hand.

18 Claims, 25 Drawing Sheets

(56) References Cited

FOREIGN PATENT DOCUMENTS

| | | |
|---|---|---|
| GB | 2237776 | 5/1991 |
| GB | 2304607 | 3/1997 |
| JP | 53113685 A | 10/1978 |
| JP | 60-12313 U | 1/1985 |
| JP | 6012313 A | 1/1994 |
| JP | 8115587 A | 5/1996 |
| JP | 9-48479 A | 2/1997 |
| JP | 2002541953 A | 12/2002 |
| JP | 2002541953 T | 12/2002 |
| JP | 2004129712 A | 4/2004 |
| JP | 2005186997 A | 7/2005 |

OTHER PUBLICATIONS

English Abstract of EP 0375579, Jun. 1990.
English Abstract of DE 202005012664, Jan. 2006.
English Abstract of DE 202004018315, Mar. 2005.

\* cited by examiner

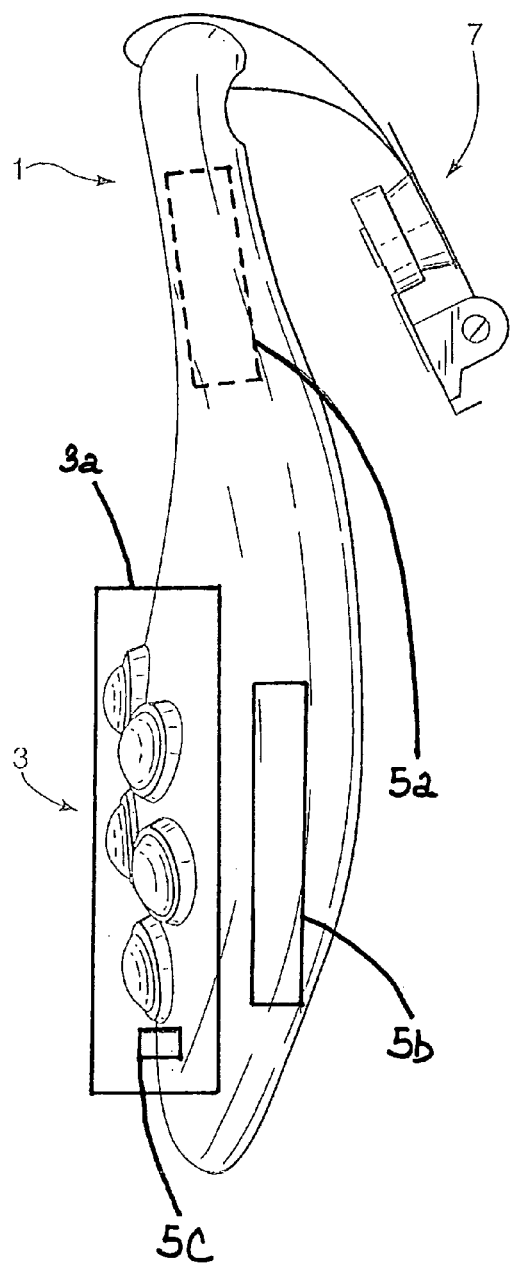
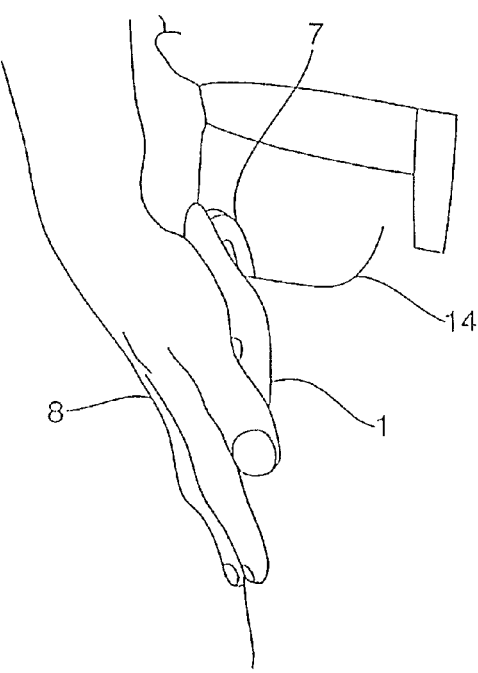

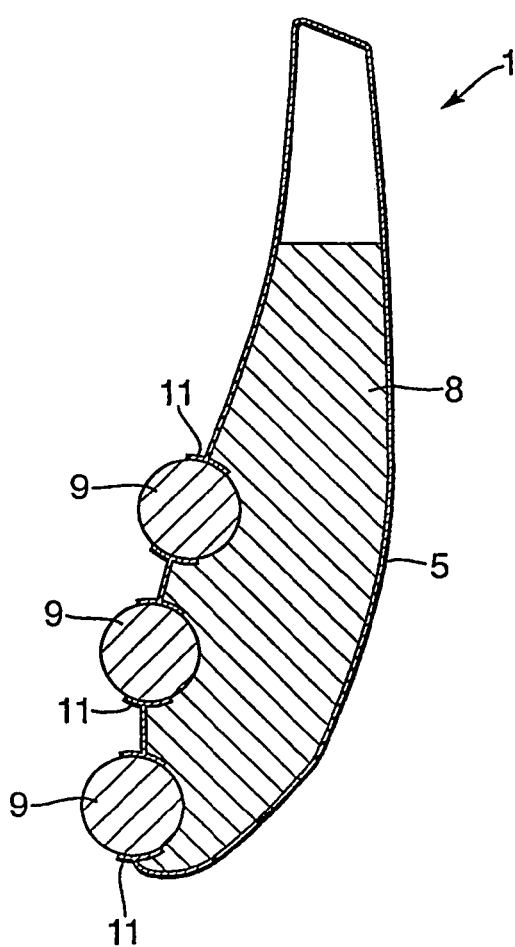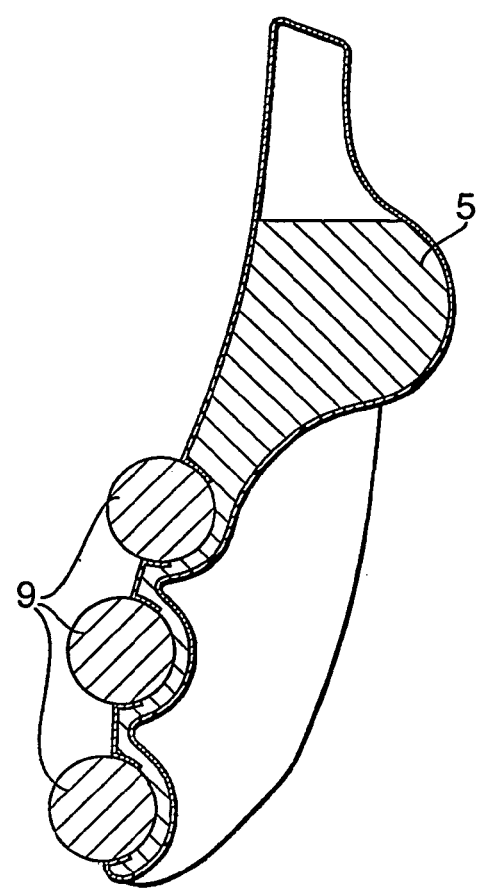

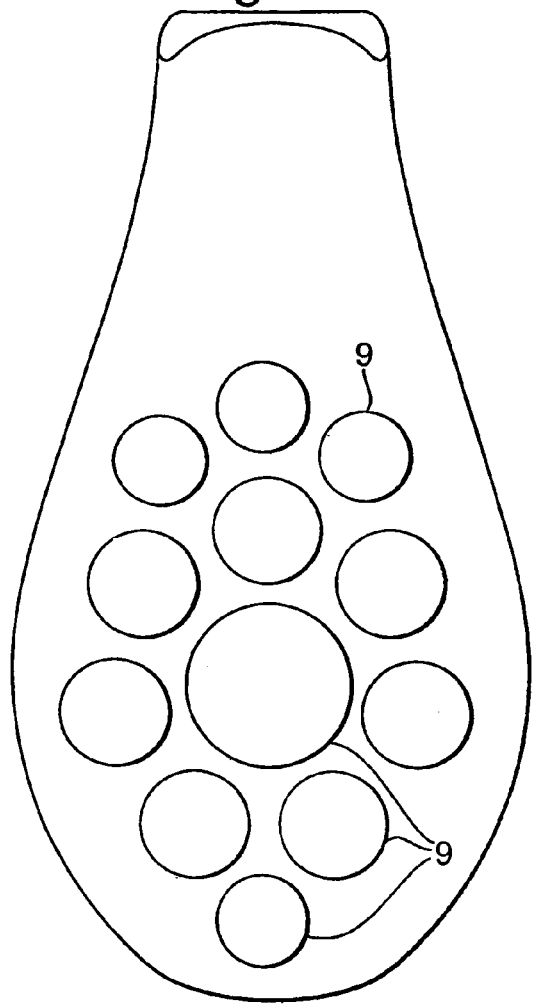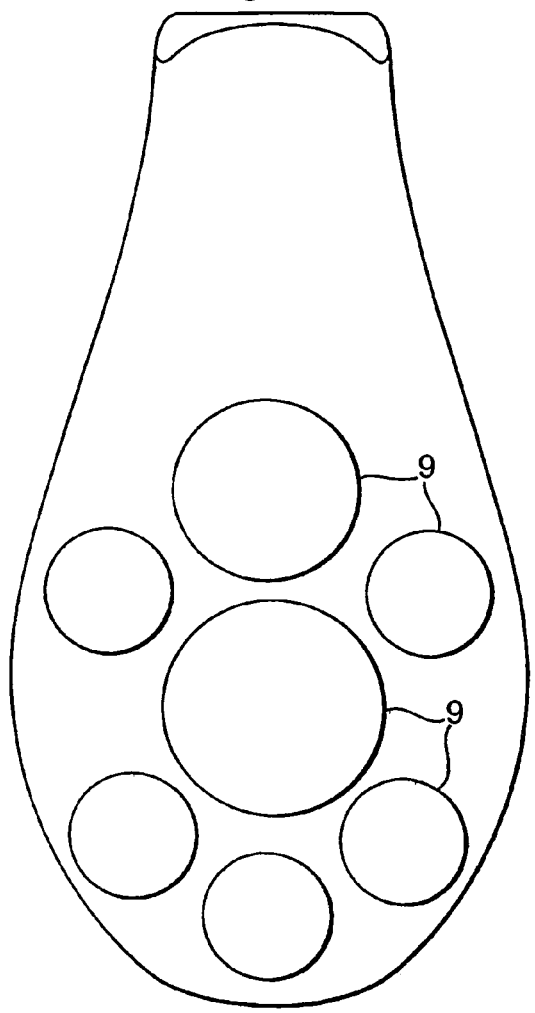

DISPENSER

BACKGROUND OF THE INVENTION

1. Field of the Invention

The present invention relates to a dispenser, and particularly, but not exclusively, to a dispenser for a hand treatment product.

2. The Prior Art

In order to prevent the spread of infectious diseases, it is required that medical staff cleanse their hands between dealing with separate patients. This may result in medical staff having to cleanse their hands many tens of times a in single working day.

Known cleansing product dispensers do not lend themselves to such frequent use. Typical dispensers are of the plunger type and require two-handed operation. One hand must be used to hold the reservoir of cleansing product while the other hand operates the plunger in order to dispense the cleaning product. Such operation may not always be convenient for staff already using one of their hands. Furthermore, such operation is relatively time consuming. These difficulties can discourage staff from cleansing their hands as often as they should, which may contribute to the spread of infection, such as MRSA.

Consequently, there is a need for a dispenser that can be operated single handedly to quickly dispense a cleanser.

SUMMARY OF THE INVENTION

The present invention provides a dispenser for dispensing a treatment product on to a hand, the dispenser comprising an applicator, and a treatment product storage reservoir in fluid communication with the applicator, wherein, in use, when a hand is moved across the applicator, treatment product is applied to the hand.

Ideally, the treatment product is a hand treatment product.

Ideally, the dispenser further comprises a restraining means for restraining the dispenser to a support surface.

The present invention is advantageous because it enables a hand treatment product to be applied to a hand without having to utilise another hand to apply it. In the present invention the support surface may be the body of a person, a wall, table or any other suitable surface.

The dispenser is capable of being operated using one hand in order to dispense the treatment product on to that hand. The dispenser is particularly suitable for use in medical environments, for example for staff to carry about their person. However, it could be used in many other areas, for example, in domestic environments such as the kitchen, workshop or garden or in commercial environments such as machine shops or automotive garages.

It is envisaged that the hand treatment product may also be suitable for treatment of skin in general and that the user may apply it with their hand to the skin on other parts of their body. For example, once the hand treatment product has been dispensed on to a user's hand, it could be applied to the user's arm.

Preferably, the applicator comprises at least one roller to apply the hand treatment product. The roller may be in the shape of a ball, for example, it may be spherical. Alternatively, the roller may be cylindrical.

The applicator may comprise one or more nozzles or brushes or a porous membrane or any other means capable of controllably applying the hand treatment product to a user's hand as the hand is moved across the applicator.

The hand treatment product may be applied directly to the applicator, e.g. the applicator may be partially immersed in the hand treatment product reservoir, or the hand treatment product may be applied indirectly to the applicator, e.g. the hand treatment product may be applied to the applicator via a porous medium such as a sponge. An example of the latter case is a sponge which may be provided within the reservoir such that when the level of hand treatment product falls below the level of the rollers the rollers will still be supplied with hand treatment product by virtue of the wicking effect of the sponge.

Preferably, the restraining means is a clip suitable for attaching the dispenser to a user, for example a spring clip of a lanyard. Alternatively, or additionally, the restraining means may be suitable for attaching the dispenser to a wall or other surface, or may be in the form of a gripping surface, for example a rubber base. If the dispenser is attached to a wall or other surface, it may be suitable for communal use.

Preferably, the dispenser is disposable. Alternatively, the reservoir may be refillable or replaceable. For example, the dispenser may be disposed of in its entirety, the reservoir may be refilled with hand treatment product, or the restraining means and/or the applicator may be retained and the reservoir replaced.

In one embodiment, the dispenser may have a cover. It is envisaged that the cover would be applied to the dispenser when it is not in use. The cover may be, for example, a hinged clam shell type or a removable fascia.

Preferably, the dispenser is colour coded to indicate for example, the nature of the hand treatment product in the reservoir, the zone of use, its ownership, or to aid association. Alternatively, the dispenser may be at least partially transparent or translucent and the hand treatment product may be colour coded.

Preferably, the dispenser may be provided with means to indicate the level of hand treatment product in the reservoir. For example, the reservoir may be transparent or translucent, either entirely or in part, so that the user can see the fluid level within it.

In certain embodiments, the reservoir may be pressurised in order to feed hand treatment product to the applicator. This may be by means of internal gas pressure, a fixed mechanical device such as a spring and piston arrangement or by means of a user applied pressure. For example, the reservoir may be manufactured from a resiliently deformable material wherein pressure applied by the user to the reservoir, for example by pressing the reservoir against their body, feeds hand treatment product to the applicator. Alternatively, hand treatment product may be fed to the applicator by gravity or capillary action.

The dispenser may be provided with a scrubbing device, for example a brush, in order to aid with the cleansing of the user's hands. The scrubbing device may be detachable and/or disposable.

The dispenser may be combined with a form of identification, for example a Radio Frequency Identification tag (RFID) or other identification card.

The dispenser may be provided with means to visually and/or audibly remind the user to use the dispenser and/or to indicate to a user that the dispenser has been used.

The dispenser may be provided with means to enable it to glow, in order to facilitate use where ambient light levels are low.

The hand treatment product may be a barrier cream or a moisturiser.

Alternatively, the hand treatment product may be a cleanser.

The cleanser may be a detergent, for example a soap, or a product containing a detergent, for example a proprietary hand cleanser such a Swarfega®.

The cleanser may be a disinfectant.

The cleanser may be an antiseptic.

The hand treatment product may contain a pharmaceutically active agent.

Preferably, the hand treatment product is a liquid. Alternatively, the hand treatment product may be a semi-solid, for example a gel, or it may be a solid. In the latter case a liquid may be obtained from the sold by the action of the applicator. For example, in the case of a roller ball applicator the rotation of the rollers against the solid cleanser will cause the cleanser to liquefy.

The hand treatment product may be an alcohol gel.

The dispenser may comprise a fluid channel for guiding treatment product to the applicator from the reservoir. A one-way valve may be provided to control fluid flow in the fluid channel. The one-way valve may allow fluid to flow from the reservoir, but prevent fluid to flow from the channel into the reservoir. The one-way valve may be positioned so that, in ordinary use of the dispenser, said one-way valve is positioned at a lower location than the applicator. A second one-way valve may be provided in the fluid channel so as to allow fluid to flow out of the channel and into the reservoir. The second valve is ideally located downstream of the first one-way valve and preferable downstream of the applicator. A wicking element may be provided in the fluid channel. The wicking element is ideally of a sponge material.

The reservoir may comprise a bulbous shaped portion located on an opposite side of the dispenser to the applicator. The bulbous shaped portion is ideally of a resiliently deformable material. Preferably, the bulbous shaped portion is of an elastically deformable material.

Preferably, the applicator comprises a plurality of rollers, the size and/or spacing of said rollers varying across the surface of the applicator.

Ideally, the surface of the or each roller is provided with an indentation for receiving and transporting treatment product from the reservoir.

The reservoir may be detachable from the remainder of the dispenser. The reservoir may comprise one or more ports for allowing fluid communication with the applicator. Means may be provide for opening said ports in response to the reservoir being secured to the remainder of the dispenser.

BRIEF DESCRIPTION OF THE DRAWINGS

Embodiments of the present invention will now be described with reference to the accompanying drawings, in which:

FIG. 3 is a side view of the first dispenser;

FIG. 4 is a perspective view of the dispenser of FIG. 1 clipped to the pocket of a user;

FIG. 5 is a cross-sectional side view of the dispenser of FIG. 1 (without an attachment clip);

FIG. 6 is a cross-sectional side view of a second dispenser, having an upper reservoir, according to the present invention;

FIGS. 10-15 each show different applicator configurations having different roller sizes and arrangements for use as a alternative to the applicator configuration shown in FIG. 1;

DETAILED DESCRIPTION OF THE PREFERRED EMBODIMENTS

Figure 1:
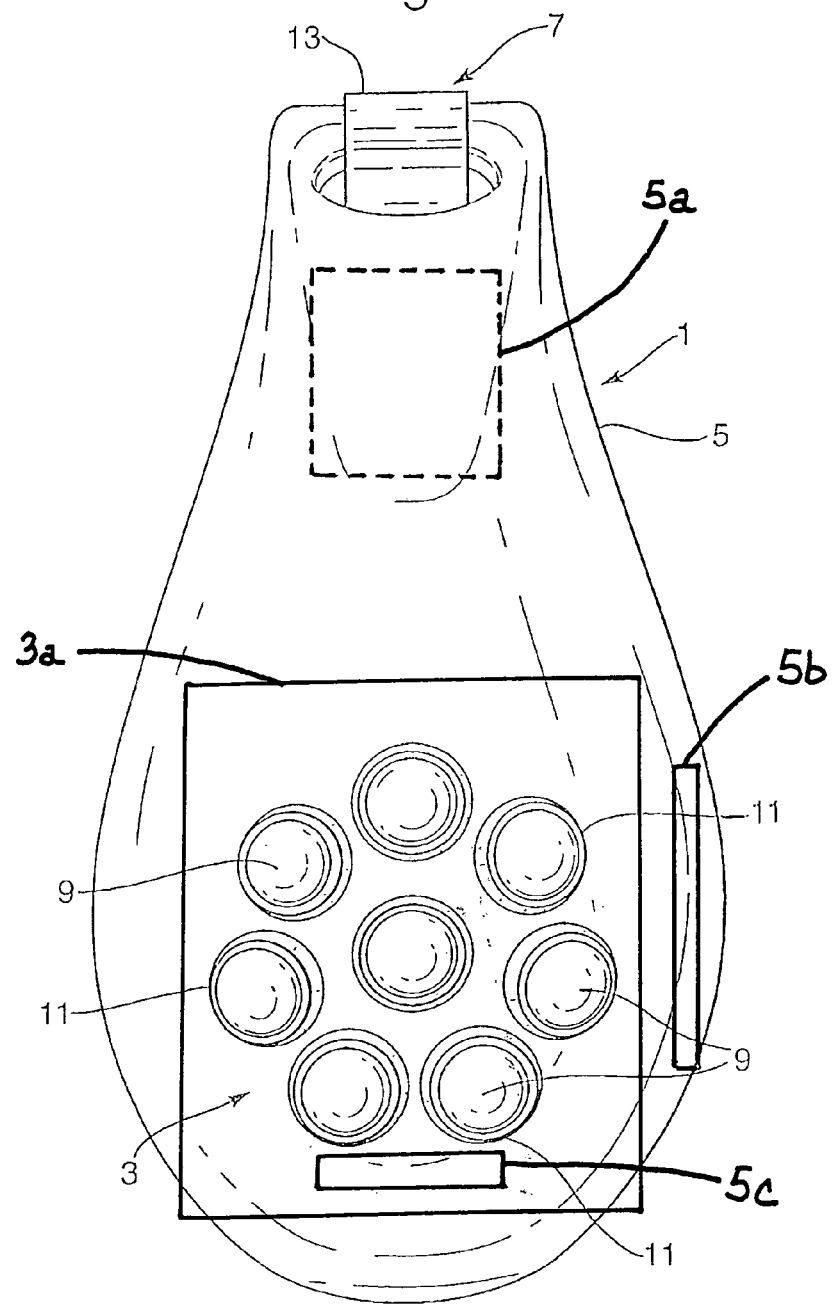
FIG. 1 is a front view of a first dispenser according to the present invention.
Figure 2:
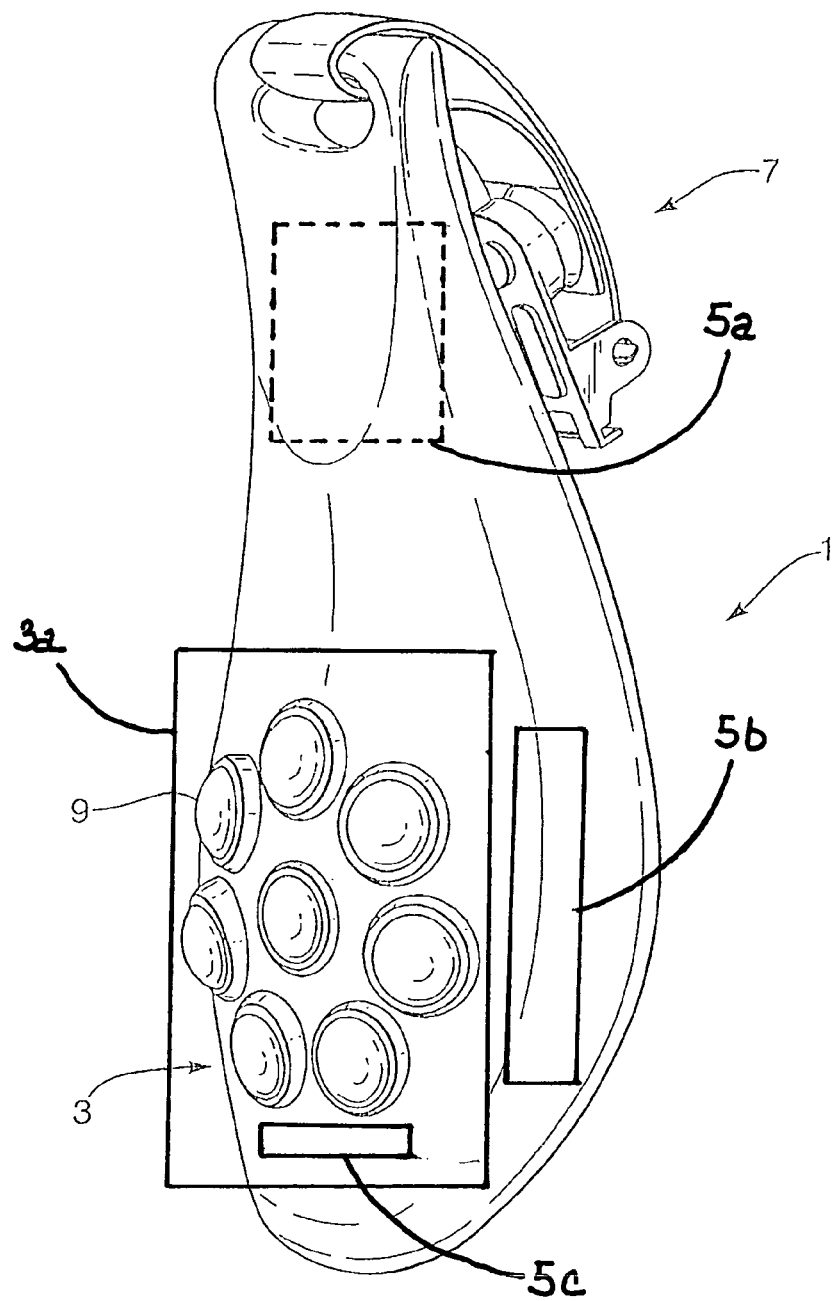
FIG. 2 is a front perspective view of the first dispenser of the present invention shown in FIG. 1.

Referring to FIG. 1, a first dispenser 1 is shown to include an applicator 3, a cover 3a, a reservoir 5 containing an alcohol gel cleanser 6, a pressurizing element 5a, a level indicating element 5b, a scrubbing element 5c, and an attachment clip 7. The applicator 3 is located on a wall of the reservoir 5 such that cleanser from the reservoir is able to pass from the reservoir to the external surface of the applicator 3 and then to the hand 8 of a user (with cover 3a removed), for example a medical staff member (see FIG. 4). The clip 7 is provided on the reservoir 5 so that, in use, the dispenser can be clipped to the user.

The applicator 3 comprises eight spherical roller balls 9 held within races 11. The roller balls 9 project inwardly through the front wall of the reservoir 5 so that at least a part of the surface of each roller ball 9 is in contact with the cleanser held therein (see FIG. 5).

In order to dispense cleanser, after removing cover 3a, the user moves their hand across the roller balls 9, wherein the roller balls 9 rotate. The internal cleanser coated surfaces of the roller balls then move outside the reservoir 5 and apply cleanser to the user's hand. Continued rotation of the roller balls 9 applies further cleanser to be applied to the user's hand in a controllable manner.

The clip 7 is attached to the top of the reservoir 5 and is hinged thereto by hinge 13. The clip 7 is located relative to the back wall of the reservoir 5 so that when the dispenser 1 is clipped to a user, for example to their belt or pocket 14, the roller balls 9 face outwardly. It is then possible for the user to single-handedly apply cleanser to their hands (see FIG. 4).

The shape/configuration of the applicator is specifically designed to ensure that as many rollers/balls as possible are kept in contact with the hand during use. In this regard, the shape/profile of the front face of the applicator is approximated by a Tanh (hyperbolic Tangent) curve.

Reservoir
General Configurations

There are three general reservoir configurations contemplated. In the first dispenser 1, the reservoir 5 is located directly behind the rollers/balls 9 (see FIGS. 1 to 5). In this case, the body of the dispenser 1 is such that it may be resiliently deformed by the user to thereby reduce the reservoir volume. Any liquid product pooling in the bottom of the reservoir 5 is then pushed upwards so as to cover the back of the rollers/balls 9. However, the following two configurations are also contemplated—

Figure 7:
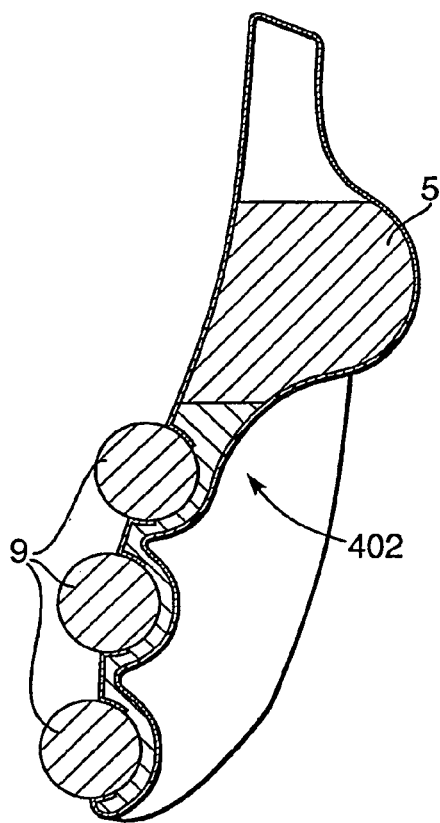
FIG. 7 is a cross-sectional side view of the second dispenser shown in FIG. 6 modified so as to incorporate a wicking element.
Figure 8:
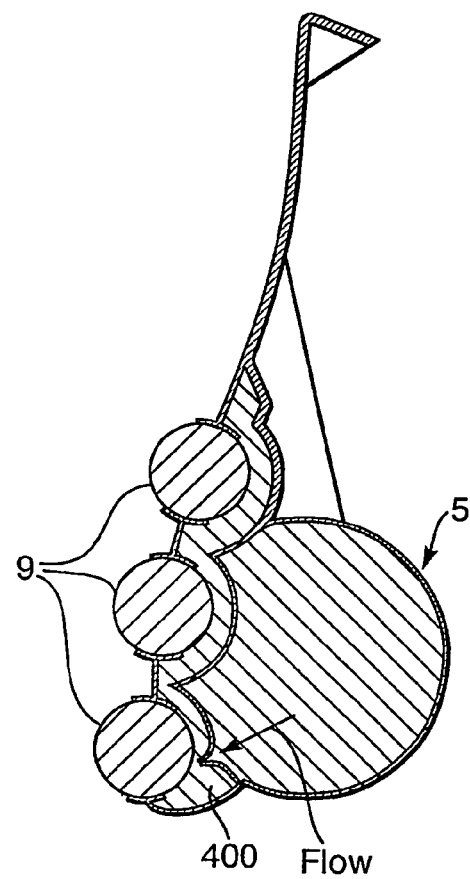
FIG. 8 is a cross-sectional side view of a fourth dispenser, having a lower reservoir and a single one-way valve, according to the present invention.

1. Upper reservoir (see FIGS. 6 and 7)—Product is stored at or near the top of the device and gravity causes it to flow down behind the rollers/balls.
2. Lower reservoir (see FIG. 8)—Product is stored at or near the bottom of the device and the force applied by the hand moving down the face causes the reservoir to be resilient deformed (compressed) so that product is pushed up behind the rollers/balls. This option may require one or more one-way valves to hold the liquid behind the rollers and prevent it from flowing back down into the reservoir. A single one-way valve is shown in FIG. 8.

Figure 9:
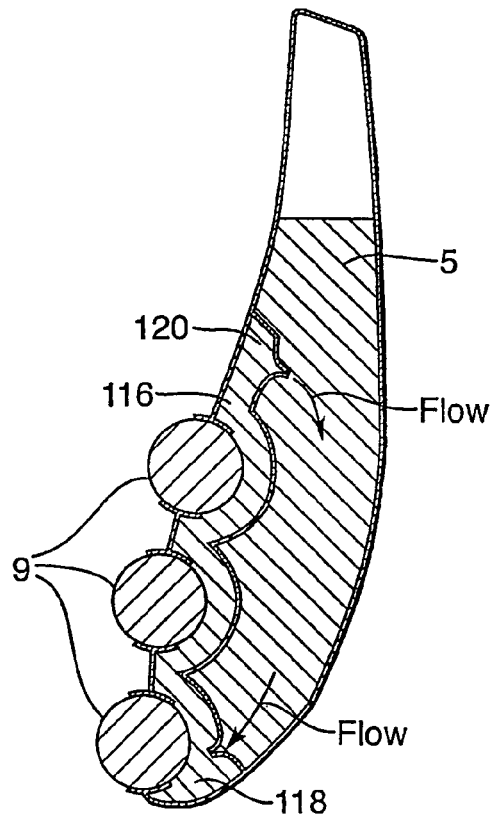
FIG. 9 is a cross-sectional side view of a fifth dispenser, having a lower reservoir and a double one-way valve, according to the present invention.
Figure 10:
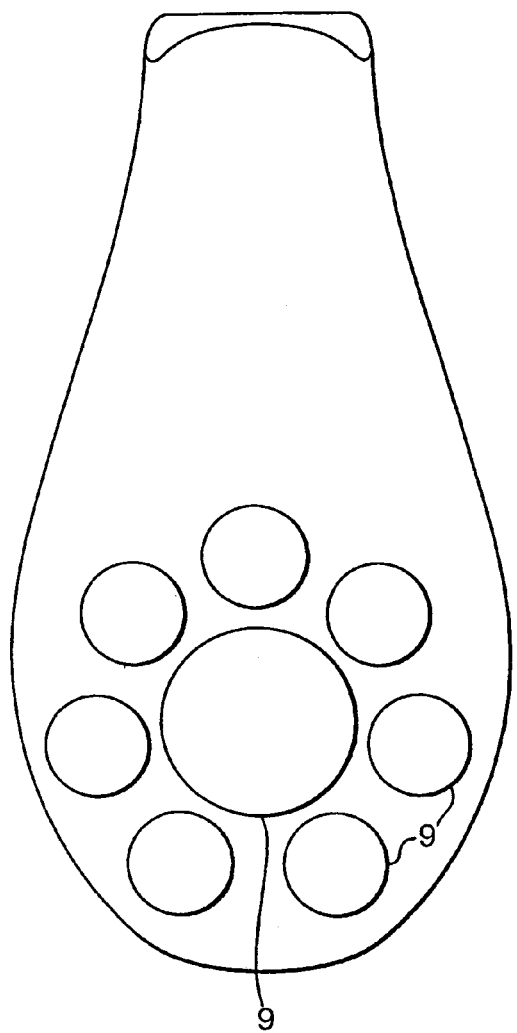
Figure 11:
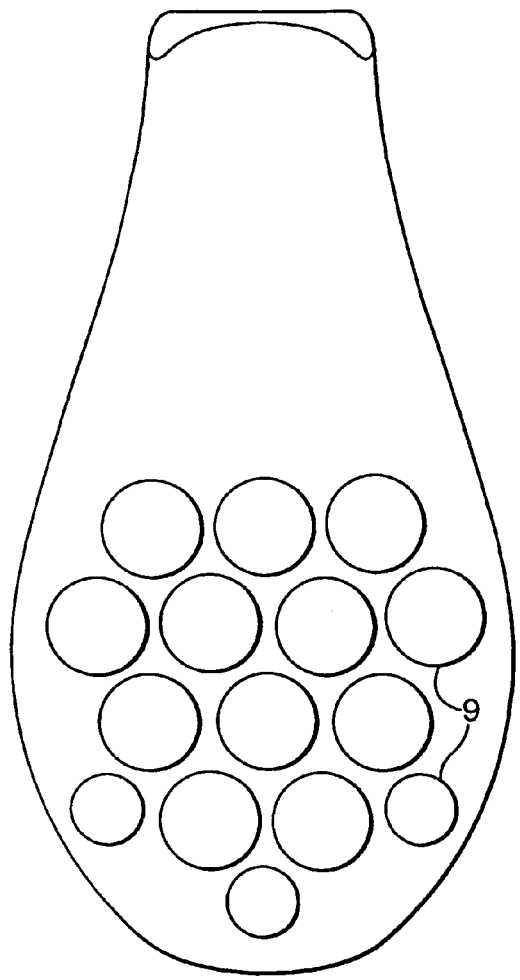
Figure 12:
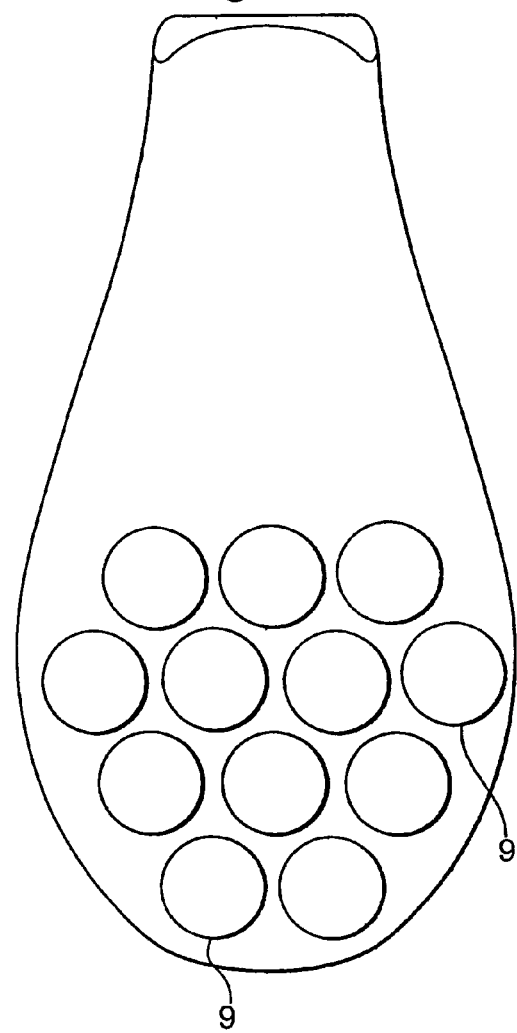
Figure 13:
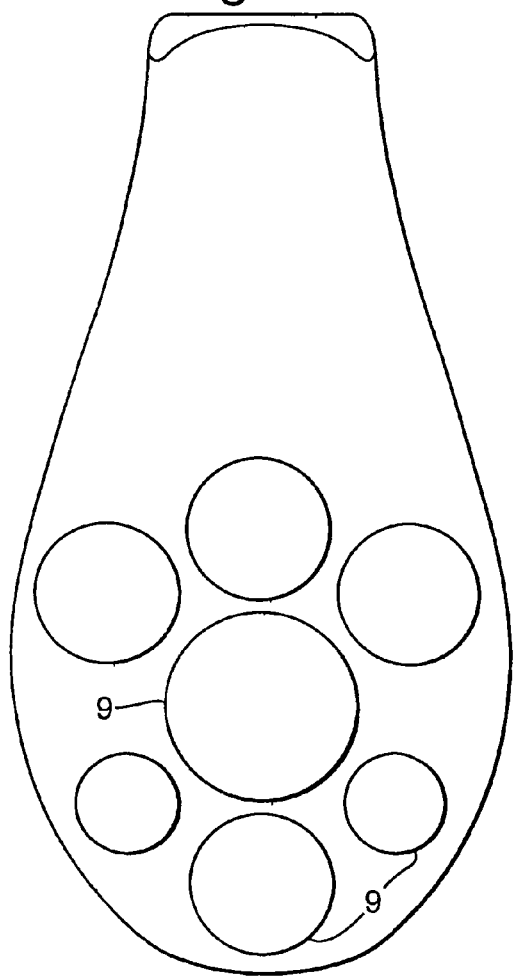

Any one of these configurations may incorporate a wicking element located in the reservoir. Ideally, the wicking element abuts the rollers 9 so as to direct liquid product onto the rollers. The wicking element makes use of capillary action to transport liquid product within the reservoir. In FIG. 7, a wicking element is provided as a sponge or open cell foam. Any one of the three configurations may include one or more one-way valves to hold the liquid behind the rollers. For example, FIG. 9 shows a reservoir located directly behind the rollers/balls 9 (as in FIGS. 1 to 5) but with a channel 116 directing liquid product on to the back of the rollers, wherein the channel is provided with a one-way inlet valve 118 (allowing flow only into the channel) and a one-way outlet valve 120 (allowing flow only out of the channel back into the resevoir).

Replaceable

Figure 34:
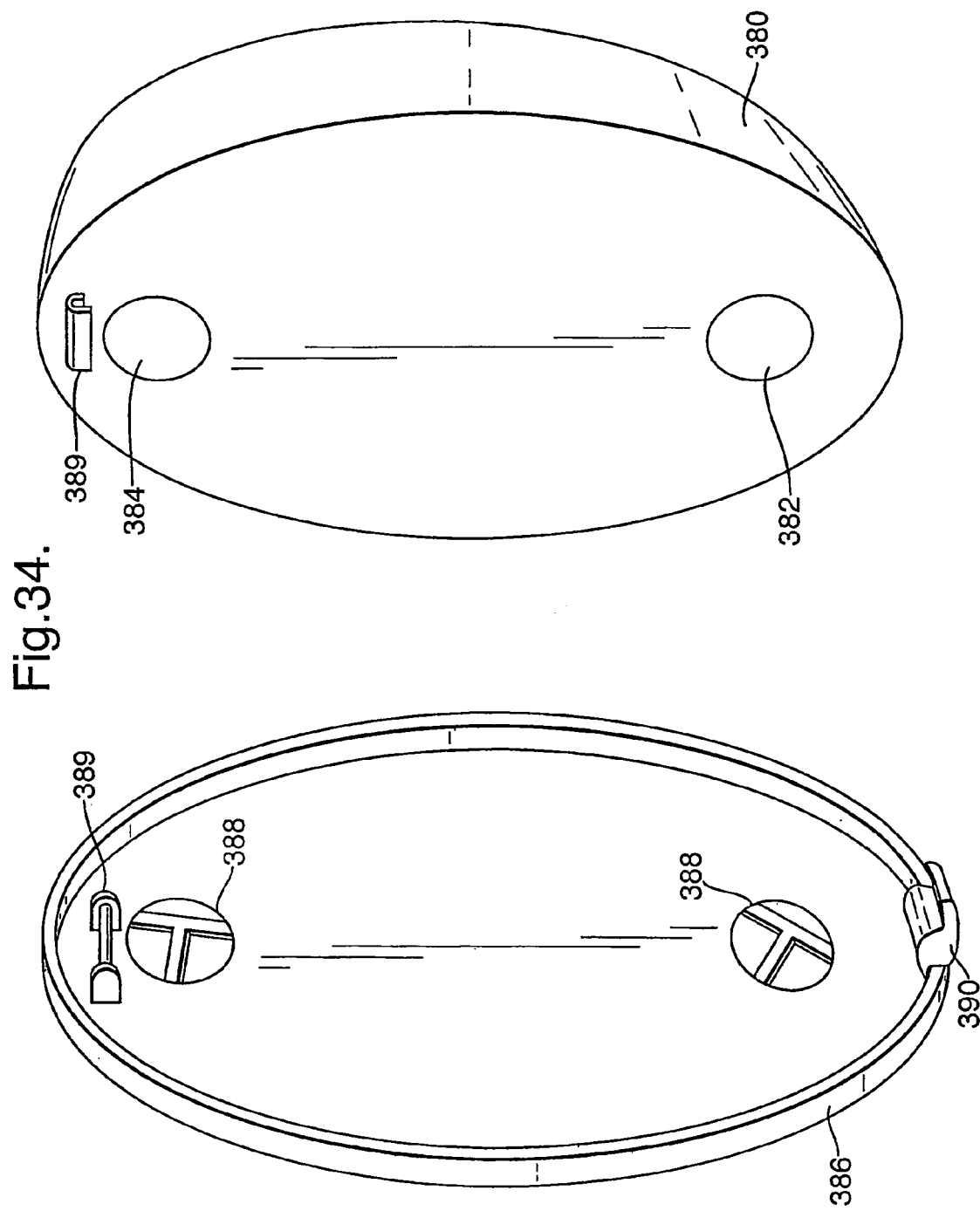
FIGS. 34 and 35 each show schematic perspective views of a removable reservoir detached and separated from a remainder of a dispenser (partly shown)
Figure 35:
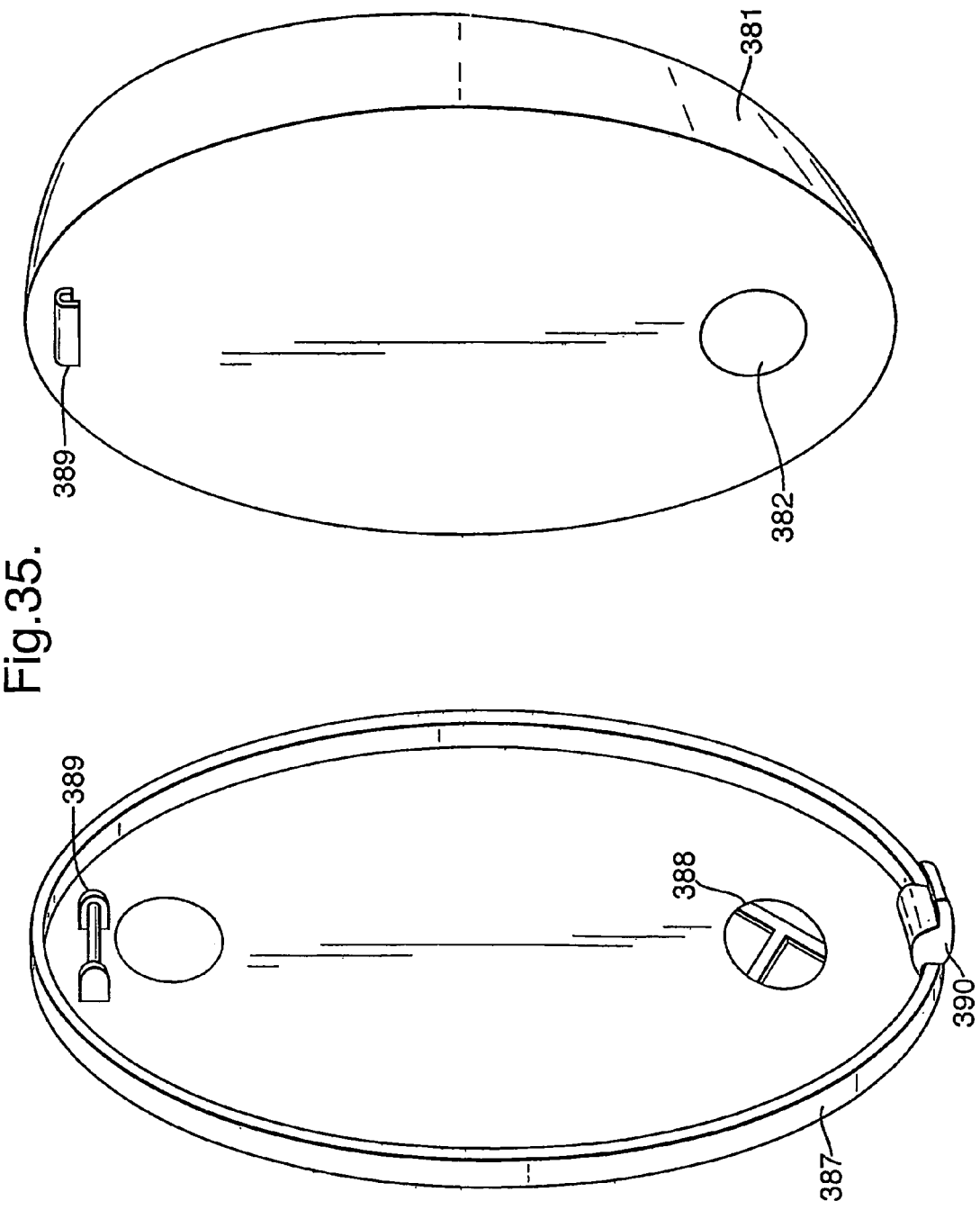

With the upper and lower reservoir configurations, it is possible to conveniently design the dispenser so that the reservoirs can be replaced once empty (see FIGS. 34 and 35). This provides a number of benefits:

1. Reduced cost of use for the customer.
2. Ease of recycling, whether immediately (re-use) or by a third party.
3. Increased flexibility, the same dispenser can be configured to deliver whichever product is required.
4. Reduced waste.
5. The effective life of a dispenser is increased.

The removable reservoir 380 of FIG. 34 comprises two frangible seals 382, 384 (and the reservoir 381 of FIG. 35 comprises just one frangible seal 382). Each seal 382, 384 is broken by an associated protrusion 388 on the dispenser body 386, 387 when the reservoir is mated with said body. In this way, fluid communication between the reservoir and the rollers is provided, even though the reservoir is sealed prior to replacement. The removable reservoir 380, 381 is secured in the mating position with the dispenser body 386, 387 by suitable means, for example, a resilient clip, and more specifically, by means of a releasable hooked hinge arrangement 389 at one end of the reservoir and dispenser body, and a resilient clip arrangement 390 at the other end thereof. The clip may comprise a hook on the dispenser body for hooking about the edge of the reservoir.

Refillable

Figure 29:
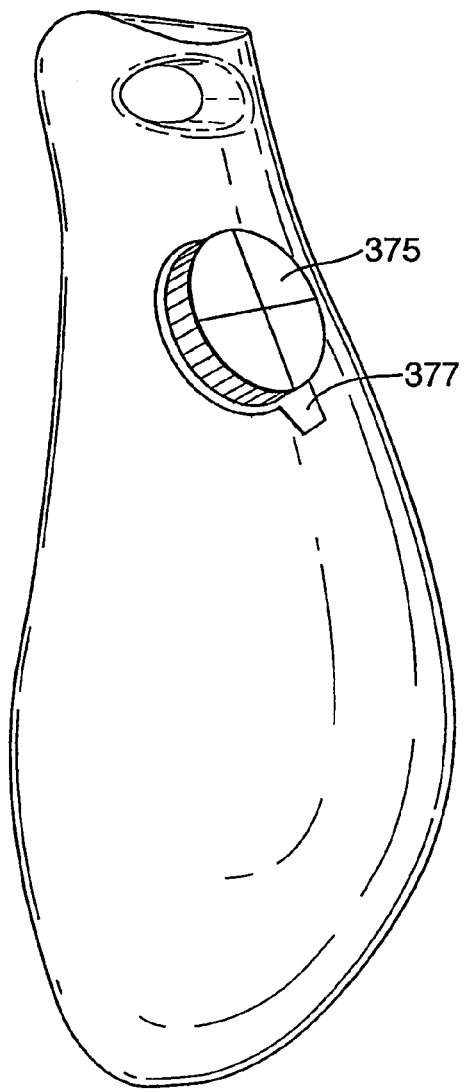
FIG. 29 shows the inlet to a dispenser reservoir sealed by means of a removable seal and a tamper evidence closure.
Figure 30:
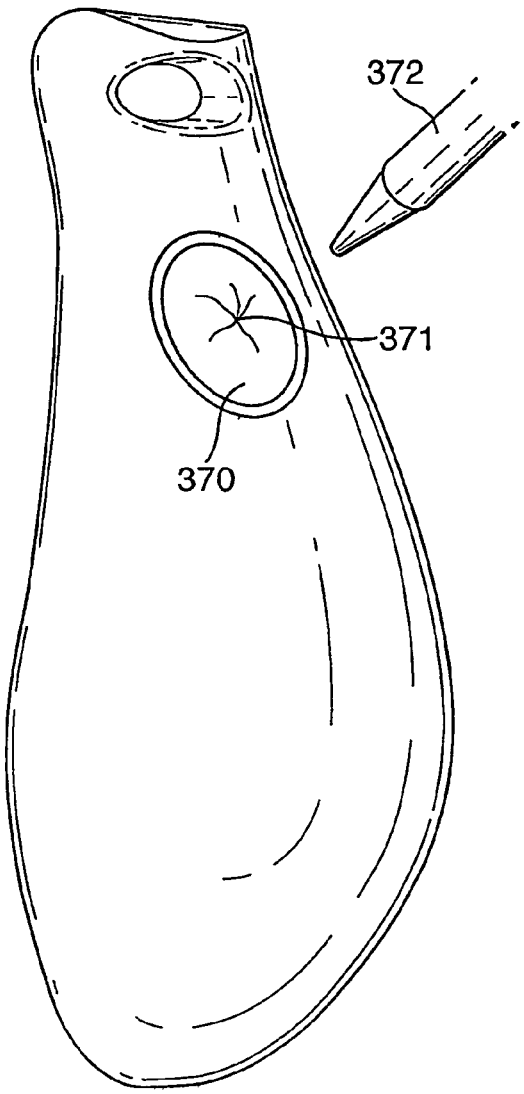
FIGS. 30 and 31 show an inlet of a dispenser reservoir sealed with a self-sealing membrane and being opened by means of a probe/device through which replacement liquid or product may be injected.
Figure 31:
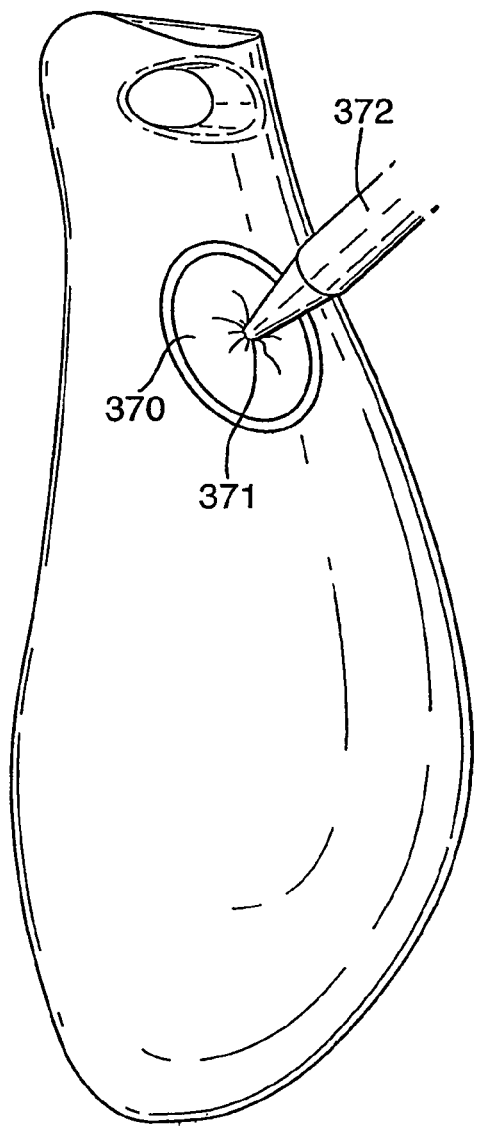
Figure 32:
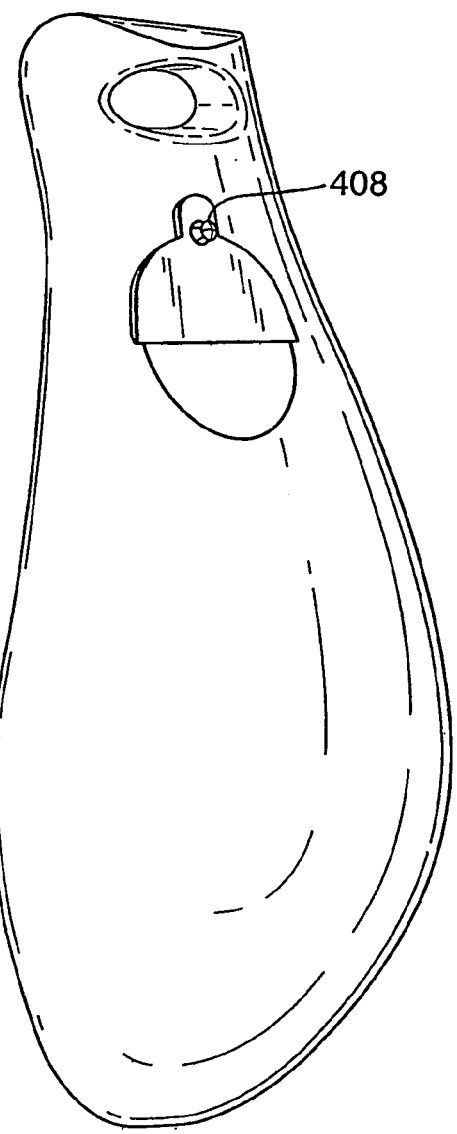
FIG. 32 shows an inlet of a dispenser reservoir sealed by means of a hinged flap retained in a closed position by means of a clip.
Figure 33:
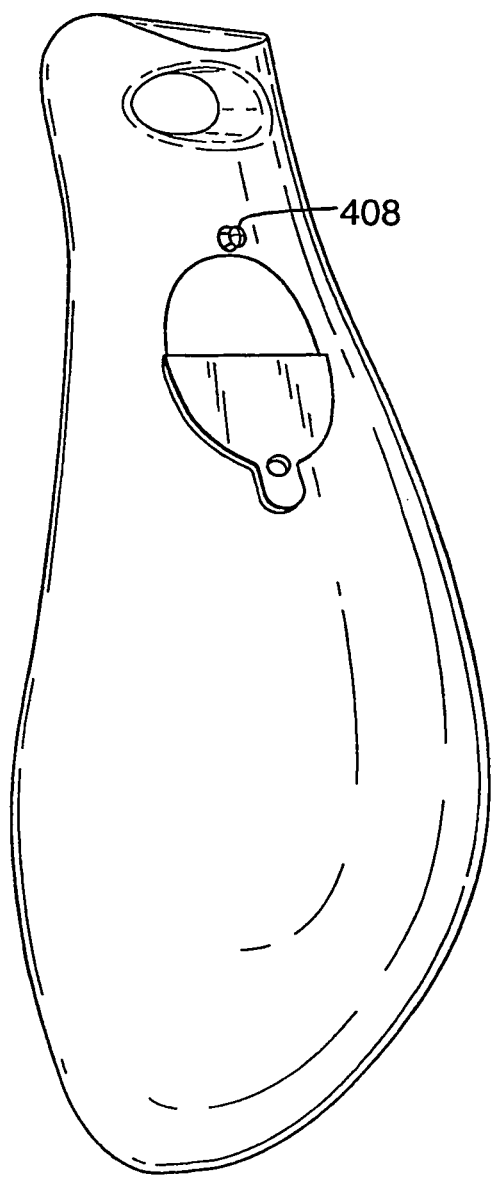
FIG. 33 shows the sealing element of FIG. 32 rotated about said hinge so as to open the reservoir inlet.

The ability to replace the reservoirs means that the dispensers are effectively refillable. However, even without a replaceable reservoir, the dispenser may incorporate one or more of the following features to allow the reservoir to be refilled:

1. Self-sealing membrane 370 (see FIGS. 30 and 31). A self-sealing membrane material is placed on the back of the dispenser. Such a mechanism typically consists of a hole 371 within a flexible resilient plastics material that is closed under normal use. By pushing a device/probe 372 into the hole, the membrane is stretched and the hole opens. Liquid can then be injected into the reservoir, the device removed and the elastic nature of the membrane causes the hole to seal.
2. One-way valve (not shown). A one-way valve may be added. This allows product into the reservoir but not out of the reservoir. In this case, the refilling device and the one-way valve may have a specific design making it difficult, if not impossible, for foreign liquids to be imparted into the reservoir.
3. Screw top (see FIG. 29). A screw closure/top 375 of a suitable size and profile may be provided to seal an inlet to the reservoir. This would enable rapid refilling via the inlet, provide additional tamper security and also offer the high resistance to failure under pressure during use.
4. Zip-lock (not shown). Here the term zip-lock refers to crimp lock self-sealing devices, such as those typically used on on freezer bags. This mechanism could be moulded directly into the body of the device, thus reducing costs. A more complex version of the crimp lock is one which contains a slider which forces the sides to seal. This type of mechanism would probably not be used as it doesn't fully seal due to the sides being separated directly under/around the slider.
5. Clip (see FIGS. 32 and 33).
6. Hook and loop fastener, or hook and hook fastener (not shown). A simple hook and loop or hook and hook system may be used. The loop/hook, or loops/hooks, could be within the end of a flap that, when unhooked, is able to be opened to access the reservoir.
7. Open hole (not shown). An open hole could be added which allows direct access into the reservoir.

Tamper Proofing

Both options for refilling and replacing the reservoir require the ability to secure the contents from tampering.

Tamper proofing a replaceable reservoir may be achieved with one or more of the following features:
1. The replaceable reservoir may have a security seal heat bonded to the opening. This seal is removed in order to allow the reservoir to be connected to the body of the dispenser. Once removed, the seal cannot be replaced. This seal, which might be a foil cover, also leaks and tears if someone tried to inject through it into the reservoir.
2. The dispenser may be provided with means for preventing access to the fluid ways in the body of the dispenser when the reservoir is removed.

Similarly, the reservoir may be provided with means for prevent access to the interior thereof when refilled. In each case, said means may operate so as to allow access in response to the reservoir being secured back into position on the dispenser body. Thus, fluid communication between the rollers and the reservoir is achieved in response to replacement of the reservoir. Such a device might comprise a spring loaded sliding door on each of the dispenser body and reservoir so as to prevent said access, wherein each door is opened when the reservoir mates with the dispenser body by means of, for example, a cam arrangement (not shown). Each sliding closes under bias of the spring when the reservoir is removed.

Figure 27:
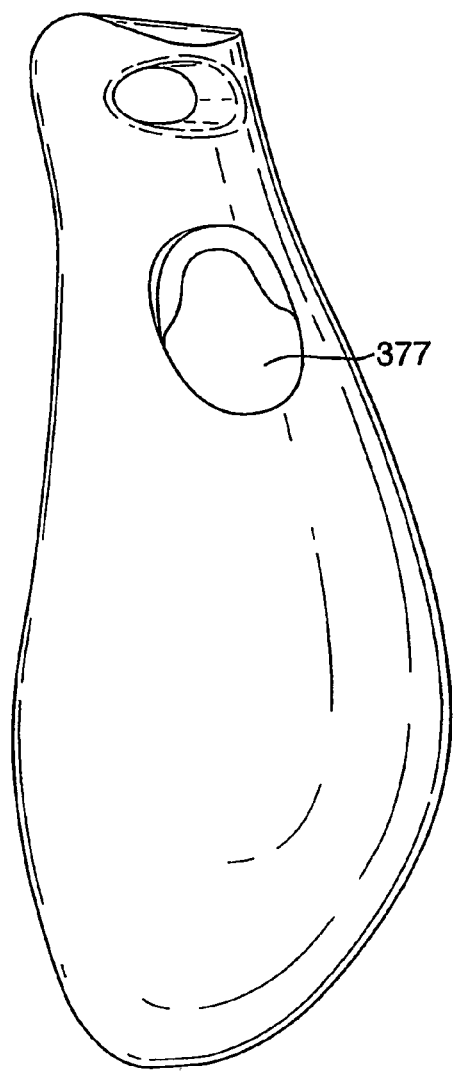
FIG. 27 shows a tamper evident seal seemingly closing an inlet port to the reservoir of a dispenser according to the present invention.
Figure 28:
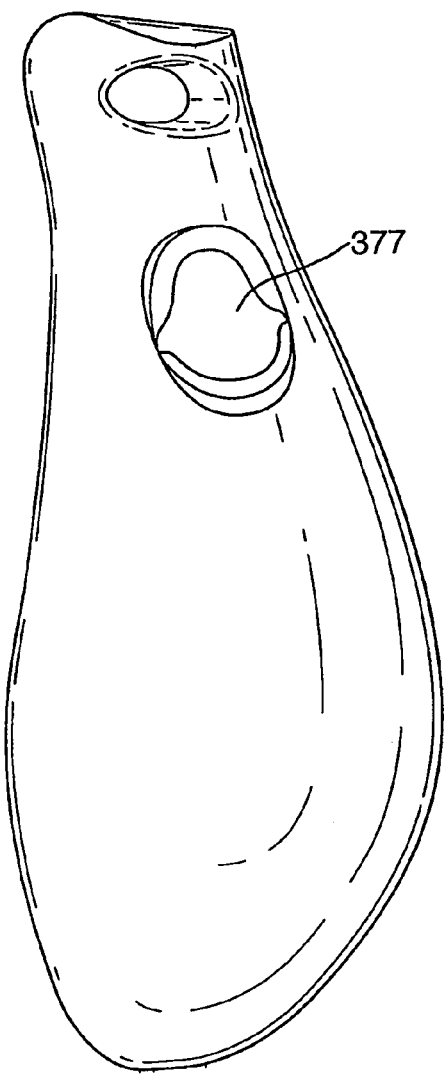
FIG. 28 shows the tamper evident seal of FIG. 27 having being folded about a hinge so as to open the inlet to the dispenser reservoir.

Tamper proofing a refillable reservoir may be achieved with one or more of the following features:
1. A sticker/cover 377 may be placed over the filling inlet port when the refill is completed (see FIGS. 27 to 29). This sticker/cover is such that, if it is removed, then it could not be replaced. It would also show signs of being punctured. Such a sticker/cover may be a membrane which is heat sealed into place. It may also be stuck in place using a contact adhesive layer.
2. In the case of the screw closure 375, the design of the closure may include a locking system wherein a frangible element of the closure is visibly damaged if the seal made by the closure is broken e.g. if the closure is rotated/unscrewed either partially or fully.
3. A coloured contact adhesive layer, or a heat sensitive adhesive layer, may be used (in the case of a zip-lock or a clip for example). Tampering with the seal would cause the colour of the adhesive to become visible and for the damage to become very obvious to the casual observer (see FIGS. 27 and 28).

Applicator

Different configurations of applicator 3 are shown in FIGS. 10 to 15. The particular configuration (roller/ball size and placement) will be selected depending on given requirements/circumstance, for example, depending on liquid product viscosity and user hand size. FIGS. 10 to 15 indicate the particular use to which the illustrated configuration is most suited. These uses are categorised with reference to Male/Female hand sizes and Low/Medium/High viscosities. A high liquid viscosity requires (a) more force to shear it, and (b) a large clearance between race and ball. As a result, a larger roller/ball is required. The opposite would be true for a low viscosity liquid, which will require a smaller roller.

In hospitals, with predominately female users, it is anticipated that a delivery of 1 ml to 1.5 ml of product will be required on each use of the dispenser. Ideally, this amount of product will be dispensed in one stroke (i.e. in one pass of the hand over the applicator). In order to achieve this, the applicator preferably comprises a cluster of eight 10 mm diameter rollers/balls.

The central roller may also be larger than the other rollers (see FIG. 10) so as to maximise use of the dispenser face and so as to provide a palm-filler.

In food preparation, with a mixed workforce, the method of use of the dispenser may vary substantially between users. Users may find that they tend to use a double swipe, they may have significantly different hadn sizes and require different doses. As a result, the rollers should be arranged differently than described above in relation to hospitals. For example, roller size may be based on the average of the male/female mix and this may result in rollers of a comparatively large size and a greater size range within a given applicator (see FIGS. 11 to 14).

In workshops and on building sites where barrier creams may be required, the higher viscosity requires a very large clearance with large rollers/balls. Also, in order to accommodate the larger male hand size/width, the dispenser may be larger as a whole and/or the rollers of the applicator be spaced from one another to a greater extent.

Figure 18:
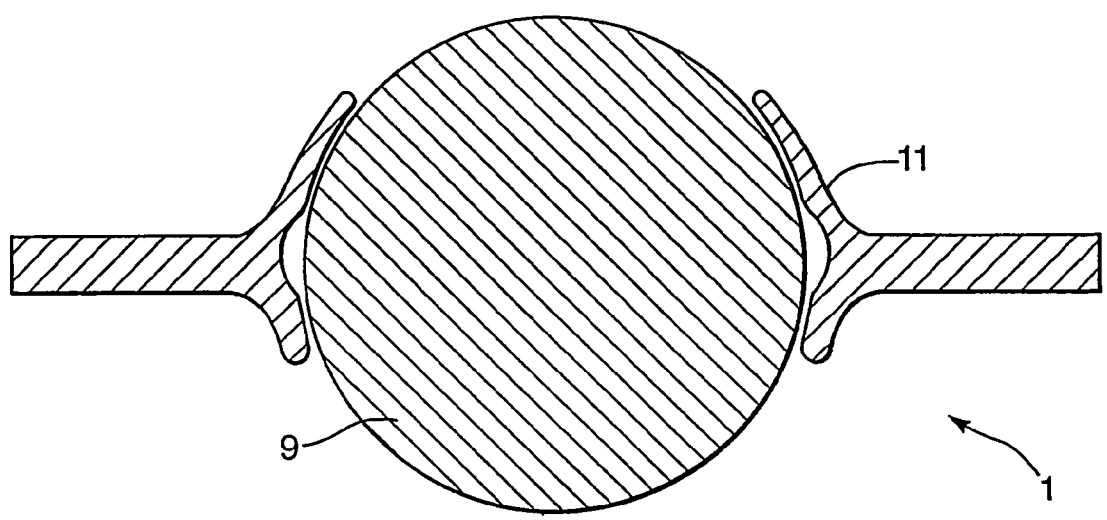
FIGS. 18 and 19 are cross-sectional side views of a roller race of a first dispenser shown in FIGS. 1-4.
Figure 19:
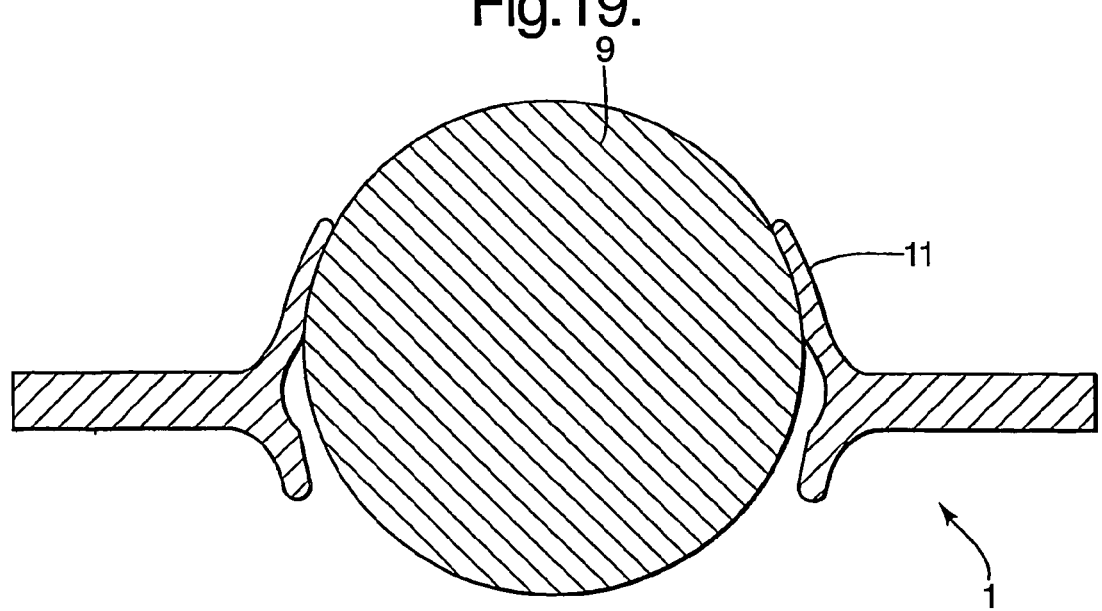
Figure 21:
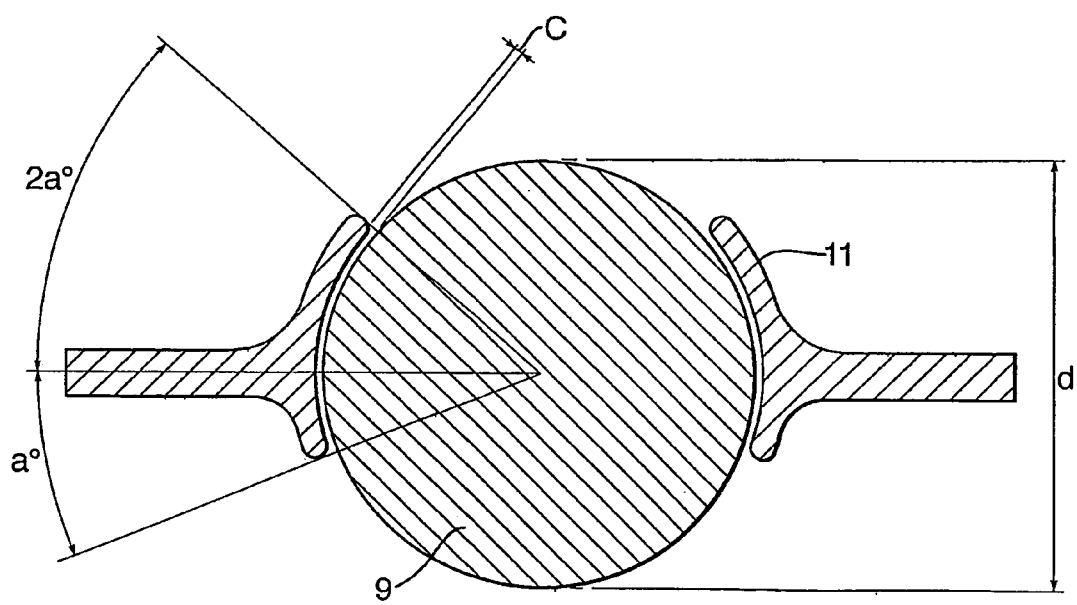
FIG. 21 is a cross-sectional view of a roller race of the first dispenser wherein the dimensions and geometry thereof are indicated.
Figure 22:
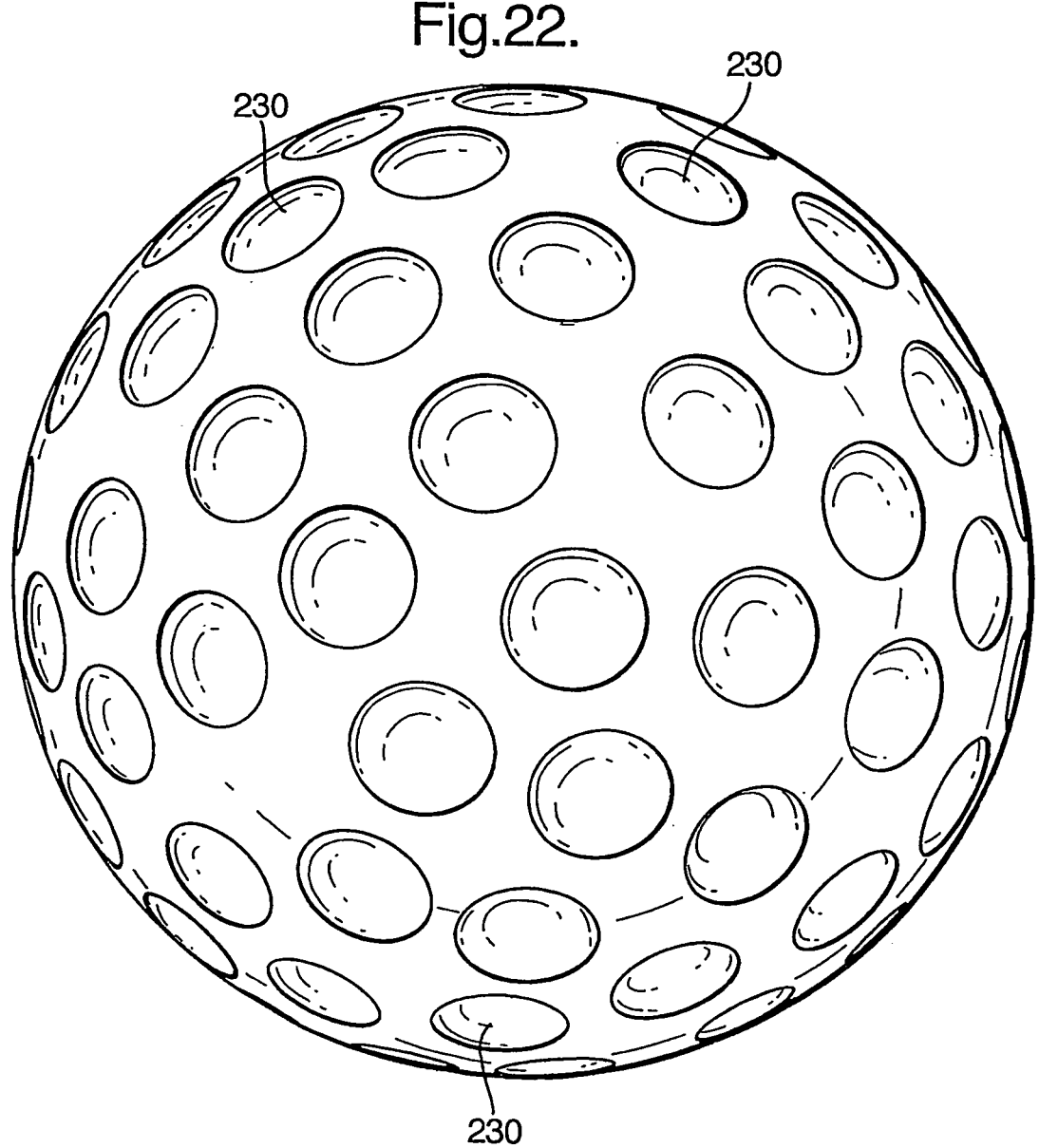
FIGS. 22-24 are perspective views of different rollers.
Figure 23:
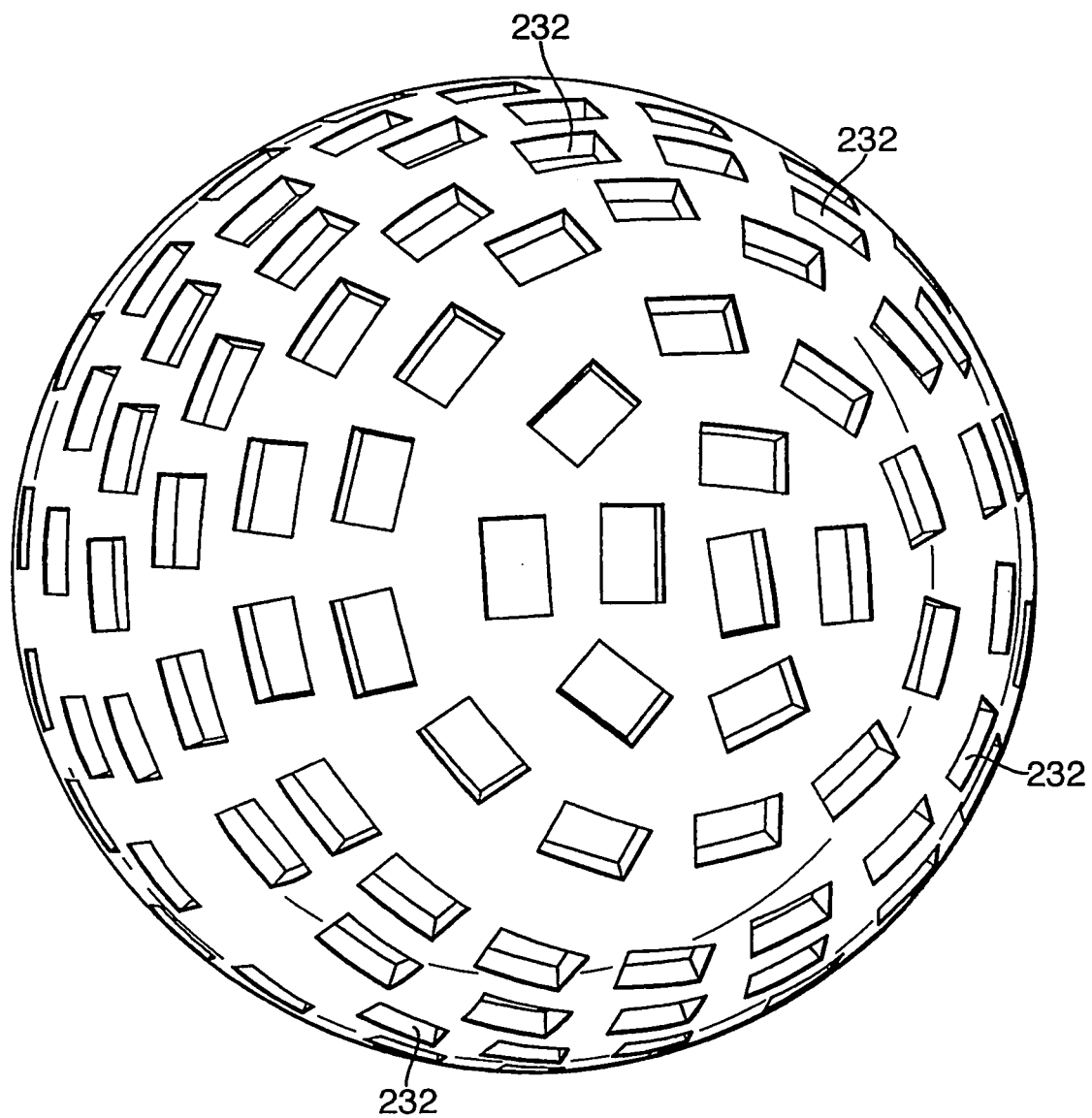
Figure 24:
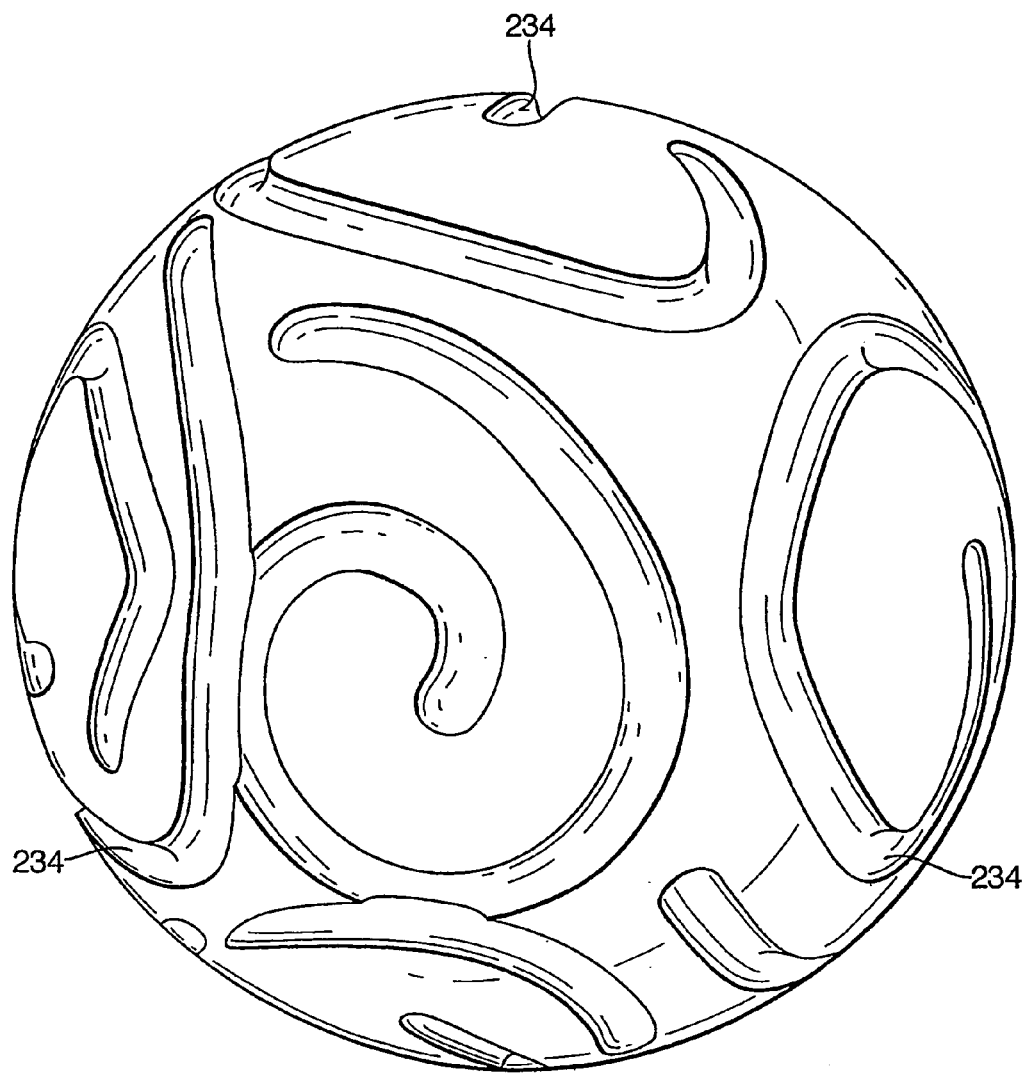
Figure 25:
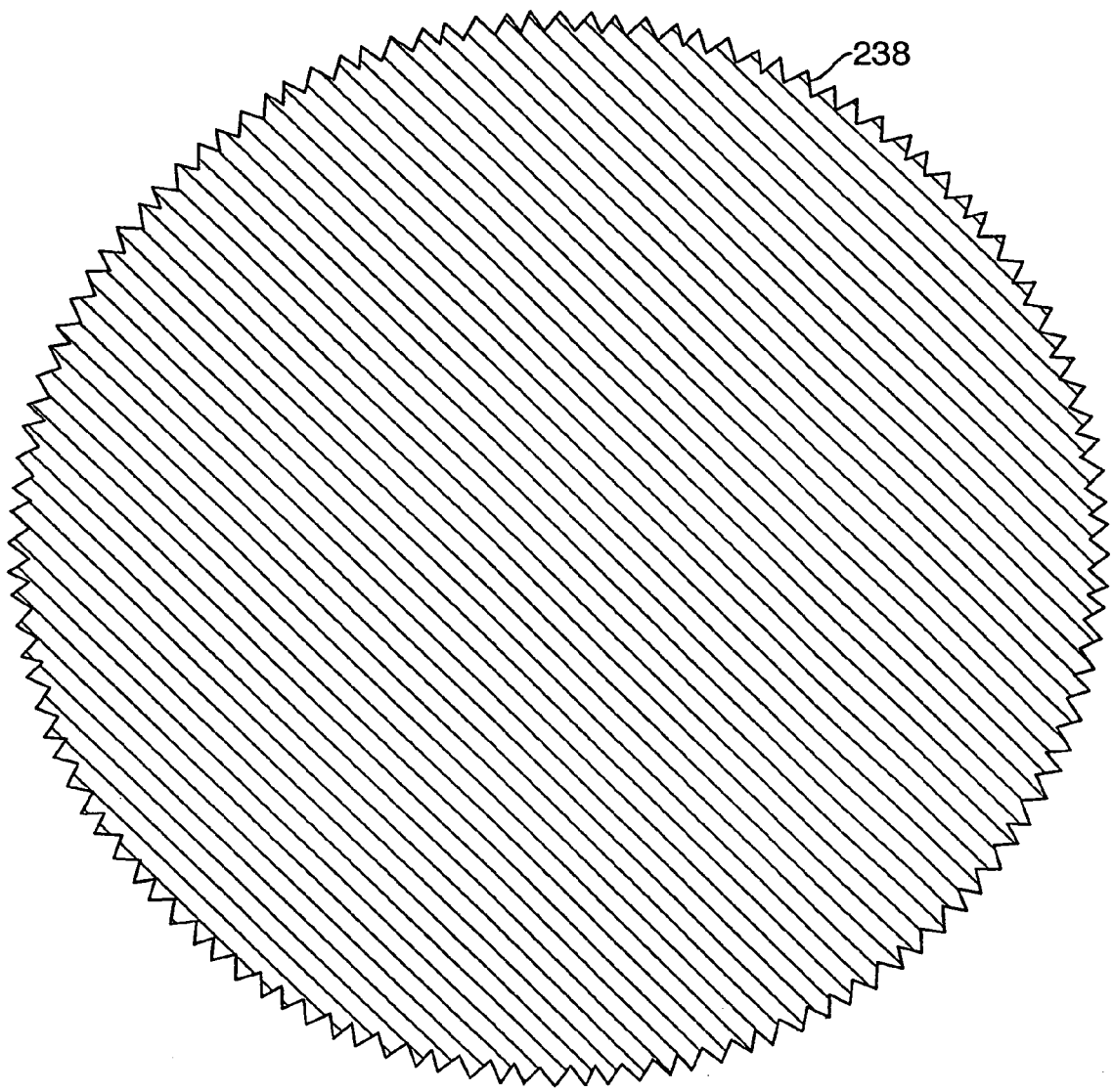
FIGS. 25 and 26 are cross-sectional views of different rollers.
Figure 26:
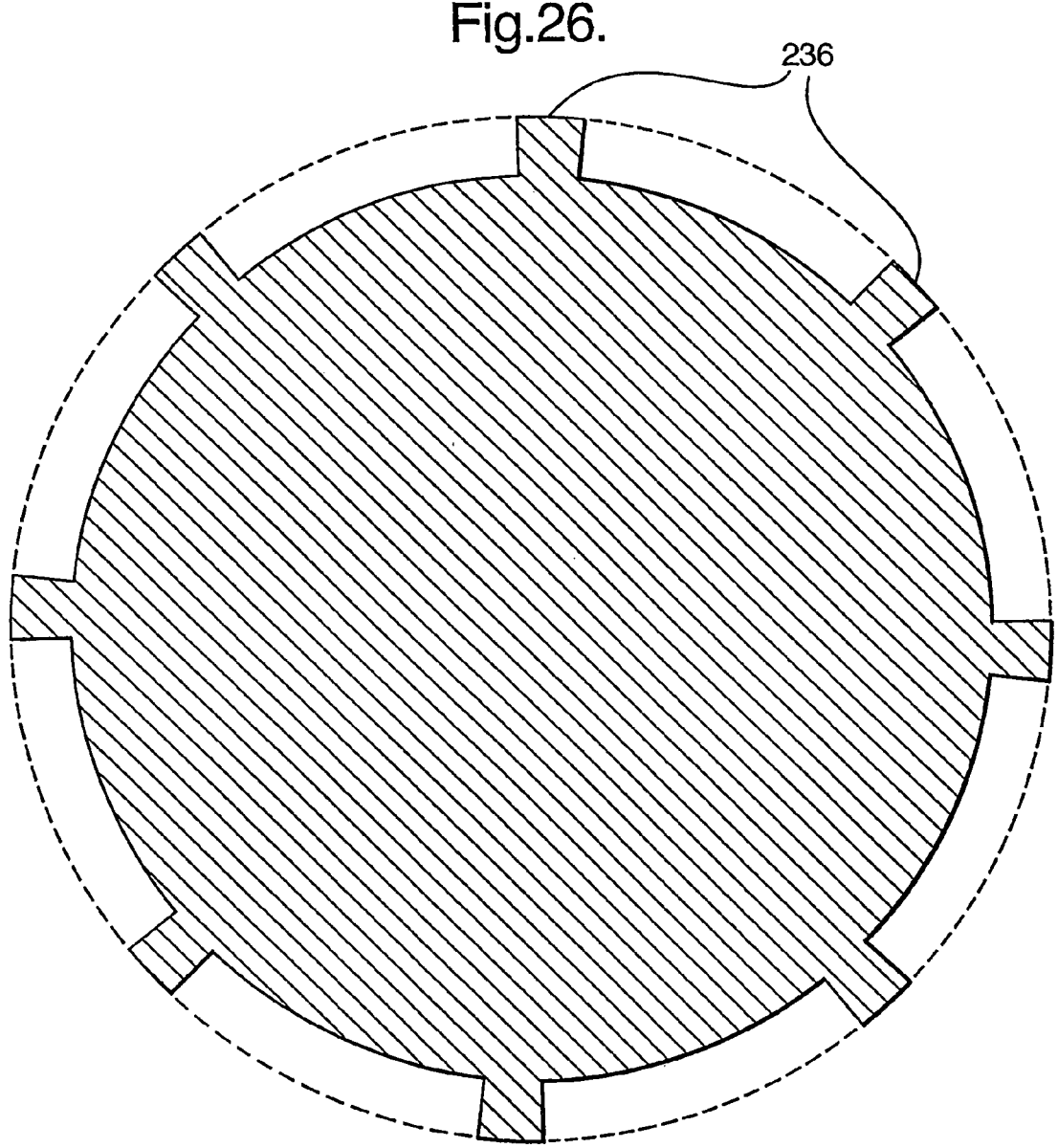

A cross-sectional side view of the standard roller 9 and roller race 11 of the first dispenser shown in FIGS. 1 to 5 is shown in FIG. 21. Ideally, the clearance (c) between a roller 9 and its associated roller race 11 is in the range of 0.1 mm to 0.24 mm. The roller diameter (d) is ideally from 5 mm to 15 mm. The possible movement of such a roller 9 within its race 11 is illustrated in FIGS. 18 and 19.

The feasibility of various roller race geometries is summarised below:

Calculation of Roller/Race Clearance

The table below shows the clearance required to deliver an amount of gel

|  |  | Radius (mm) | | | | | | | | | | | | | |
| --- | --- | --- | --- | --- | --- | --- | --- | --- | --- | --- | --- | --- | --- | --- | --- |
|  |  | 2 | 3 | 4 | 5 | 6 | 7 | 8 | 9 | 10 | 11 | 12 | 13 | 14 | 15 |
| Number of balls | 1 | 3.33 | 2.22 | 1.67 | 1.33 | 1.11 | 0.95 | 0.83 | 0.74 | 0.67 | 0.61 | 0.56 | 0.51 | 0.48 | 0.44 |
|  | 2 | 1.67 | 1.11 | 0.83 | 0.67 | 0.56 | 0.48 | 0.42 | 0.37 | 0.33 | 0.30 | 0.28 | 0.26 | 0.24 | 0.22 |
|  | 3 | 1.11 | 0.74 | 0.56 | 0.44 | 0.37 | 0.32 | 0.28 | 0.25 | 0.22 | 0.20 | 0.19 | 0.17 | 0.16 | 0.15 |
|  | 4 | 0.83 | 0.56 | 0.42 | 0.33 | 0.28 | 0.24 | 0.21 | 0.19 | 0.17 | 0.15 | 0.14 | 0.13 | 0.12 | 0.11 |
|  | 5 | 0.67 | 0.44 | 0.33 | 0.27 | 0.22 | 0.19 | 0.17 | 0.15 | 0.13 | 0.12 | 0.11 | 0.10 | 0.10 | 0.09 |
|  | 6 | 0.56 | 0.37 | 0.28 | 0.22 | 0.19 | 0.16 | 0.14 | 0.12 | 0.11 | 0.10 | 0.09 | 0.09 | 0.08 | 0.07 |
|  | 7 | 0.48 | 0.32 | 0.24 | 0.19 | 0.16 | 0.14 | 0.12 | 0.11 | 0.10 | 0.09 | 0.08 | 0.07 | 0.07 | 0.06 |
|  | 8 | 0.42 | 0.28 | 0.21 | 0.17 | 0.14 | 0.12 | 0.10 | 0.09 | 0.08 | 0.08 | 0.07 | 0.06 | 0.06 | 0.06 |
|  | 9 | 0.37 | 0.25 | 0.19 | 0.15 | 0.12 | 0.11 | 0.09 | 0.08 | 0.07 | 0.07 | 0.06 | 0.06 | 0.05 | 0.05 |
|  | 10 | 0.33 | 0.22 | 0.17 | 0.13 | 0.11 | 0.10 | 0.08 | 0.07 | 0.07 | 0.06 | 0.06 | 0.05 | 0.05 | 0.04 |
|  | 11 | 0.30 | 0.20 | 0.15 | 0.12 | 0.10 | 0.09 | 0.08 | 0.07 | 0.06 | 0.06 | 0.05 | 0.05 | 0.04 | 0.04 |
|  | 12 | 0.28 | 0.19 | 0.14 | 0.11 | 0.09 | 0.08 | 0.07 | 0.06 | 0.06 | 0.05 | 0.05 | 0.04 | 0.04 | 0.04 |

-continued

| | Radius (mm) | | | | | | | | | | | | | |
|---|---|---|---|---|---|---|---|---|---|---|---|---|---|---|
| | 2 | 3 | 4 | 5 | 6 | 7 | 8 | 9 | 10 | 11 | 12 | 13 | 14 | 15 |
| 13 | 0.26 | 0.17 | 0.13 | 0.10 | 0.09 | 0.07 | 0.06 | 0.06 | 0.05 | 0.05 | 0.04 | 0.04 | 0.04 | 0.03 |
| 14 | 0.24 | 0.16 | 0.12 | 0.10 | 0.08 | 0.07 | 0.06 | 0.05 | 0.05 | 0.04 | 0.04 | 0.04 | 0.03 | 0.03 |
| 15 | 0.22 | 0.15 | 0.11 | 0.09 | 0.07 | 0.06 | 0.06 | 0.05 | 0.04 | 0.04 | 0.04 | 0.03 | 0.03 | 0.03 |

Assumptions:
1 Perfect volumetric displacement occurs
2 The effectiveness of the clearance is not a function of the radius of the ball pi=3.141593
Volume dispensed (mm3)
1000
Useful contact area
75%
Length of stroke (mm)
100

| Conditional formatting ranges | | | |
|---|---|---|---|
| | Upper | Lower | |
| Left hatch | 30 | 0.5 | Potentially too much clearance for this to work |
| White | 0.5 | 0.25 | May work with this amount of clearance |
| Right hatch | 0.25 | 0.08 | Will work with this amount of clearance |
| Speckled | 0.08 | 0 | Potentially not enough clearance for this to work |

It will be understood that pressure within the reservoir (generated by compressing the reservoir by pressing on the face of the dispenser) does not force liquid product out of the container, as flow is choked around the roller balls. Additional pressure makes no difference to the amount of liquid dispensed. Instead, the pressure applied is used to force liquid product into the area around the rollers.

Figure 16:
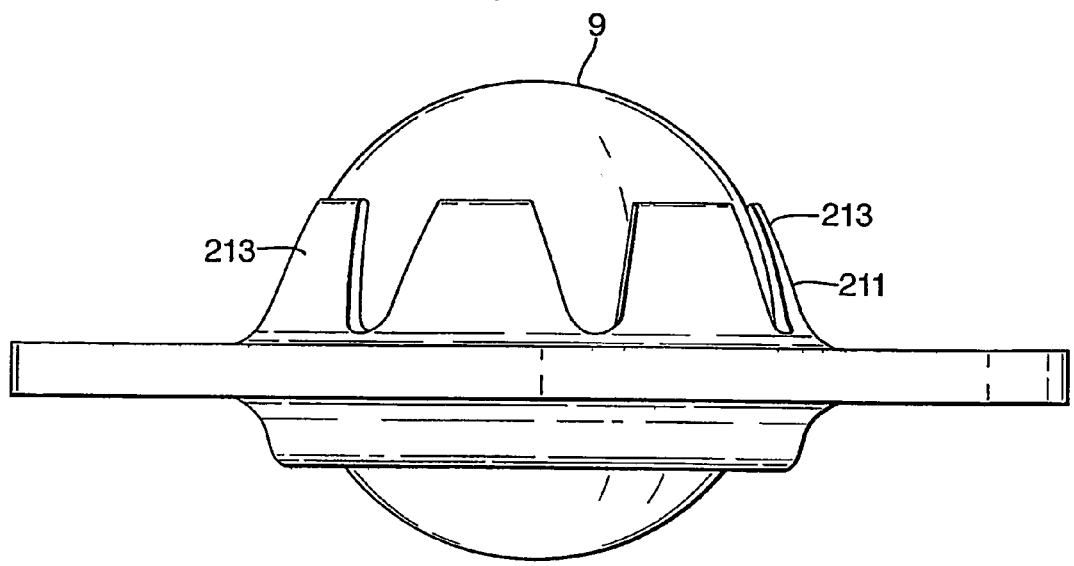
FIGS. 16 and 17 are side views of an alternative roller race which allows a passage of liquid product without any four roller rotations.
Figure 17:
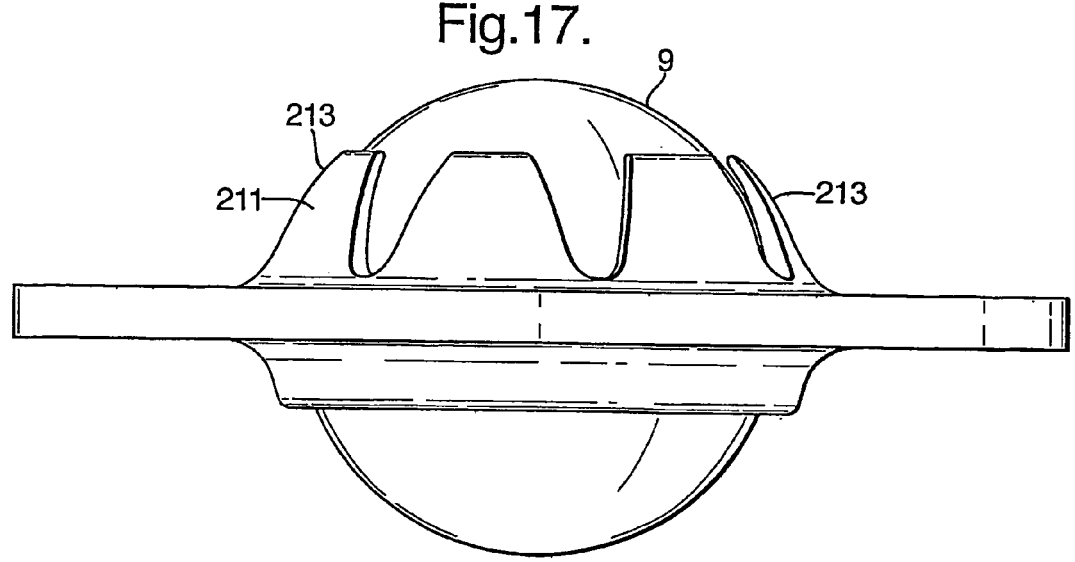
Figure 20:
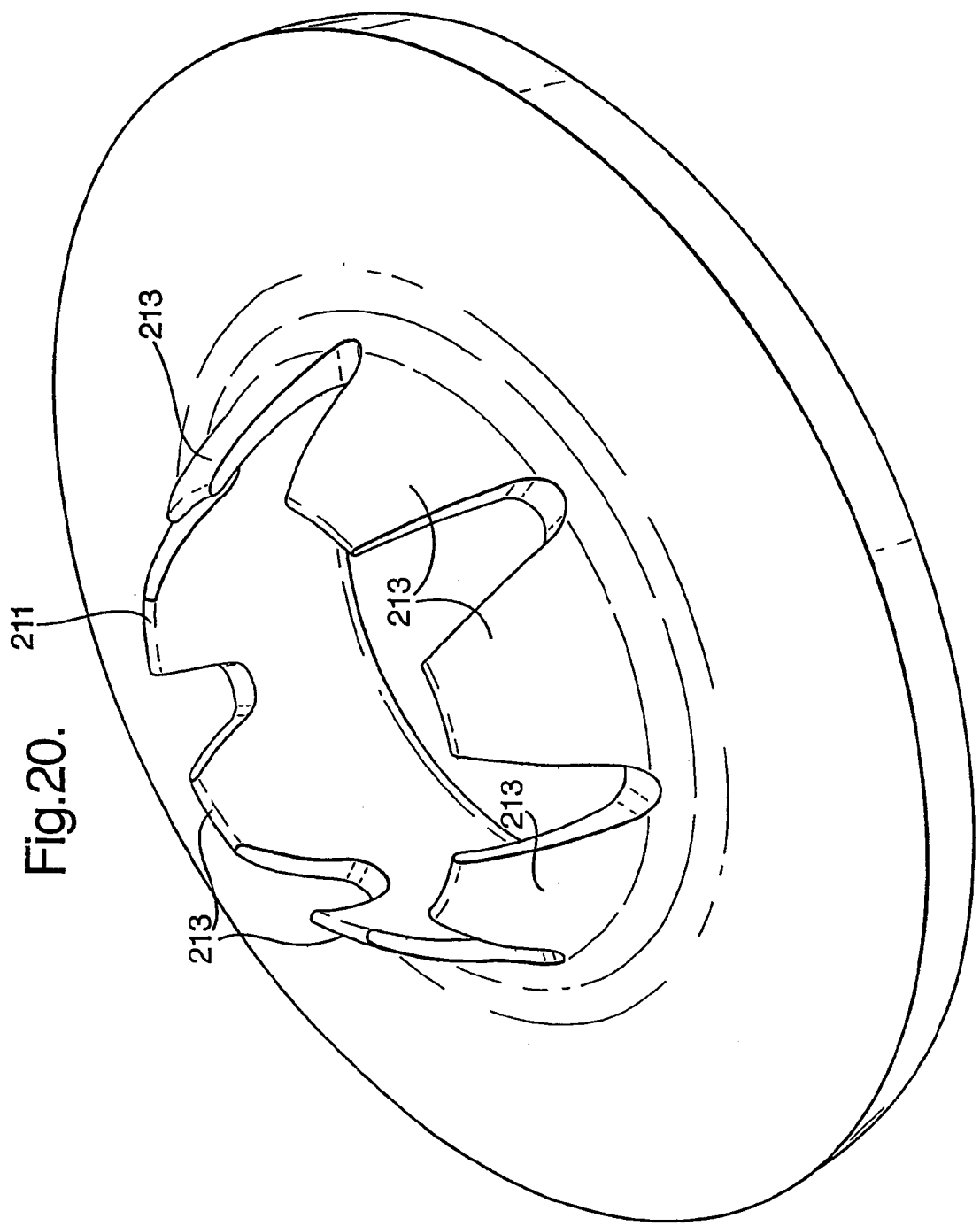
FIG. 20 is a perspective view of a roller race as shown on FIGS. 16 and 17.

Nevertheless, in contrast, a modified roller race 211 is shown in FIGS. 16, 17 and 20. This modified roller race 211 has material removed so as to provide a plurality of circumferentially spaced upstanding race elements 213. The arrangement is such that the roller and race combination acts as a pressure responsive valve.

In this respect, if pressure is sufficiently great within the reservoir, then the roller is moved within the race and product is able to flow between said upstanding race elements 213 and thereby exit the reservoir in addition to doing so by means of roller rotation. In other words, if the reservoir pressure is sufficient, then product may exit the reservoir through the roller race 211 without the need for the roller 9 to rotate. This prevents potential damage to the reservoir due to high internal pressures.

Roller Composition

The rollers/balls may be made of different materials to support the transfer of fluids and help in differentiating the contents. These compositions might include:

1. Solid core with a porous shell may be used to transfer a greater quantity of product.
2. Thermochromic dye may be used to tell the user when the liquid is within its effective operation temperature. This would be used for liquids that denature or breakdown above a certain temperature. It could also be used if a temperature dependant solid, or semi-solid, is used instead of a liquid. Furthermore, it could be an indication of bacteria growth (i.e. that the temperature at which bacteria grows has been achieved), thus encouraging users to clean their hands.
3. Thermal expansion. In a case where the contents to be dispensed becomes inactive above a certain temperature, the balls could be made from a material which expands to prevent dispensing above that temperature.
4. Fragrance additives. These may be added to the reservoir contents or to the material making up the roller/ball. This would be done to stimulate the reward mechanism on use.
5.
5. The rollers may be either transparent and/or hollow to enhance the aesthetics of the dispenser design.
6. Colour may be used to enhance the design or to signify what type of product is contained within in the device.
7. A product reactive surface such a hygroscopic dye may be used to indicate when the balls have fluid on them and thus when they are operating efficiently.
8. A deformable material, such as a sponge, may be used to help pump the contents from the reservoir as well as transmit it via rolling. The roller itself may be of a sponge material.
9. Materials. The rollers/balls may have a material surface to improve the feel and make them appear softer.

Roller Surface

A number of preferred surface arrangements for the rollers/balls are shown in FIGS. 22 to 26 of the accompanying drawings. All of these are designed to either increase the ability of the dispenser to deliver product from the reservoir or to enhance the feel of the device. Different surfaces include:

1. Dimples such as those on a golf ball. These dimples increase the volume able to be dispensed for a given race clearance. This surface may be used for low viscosity liquids to reduce leakage.
2. Dimples/indentations/groves of different shapes e.g. round dimples 230 (see FIG. 22), square/rectangular dimples 232 (see FIG. 23), curved groove lines 234 (see FIG. 24). These dimples/indentations/groves may be of different depths and all be provided on the same roller.
3. Fencing 236 (see FIG. 236), where the majority of the surface is below the outer limits, could be used for high viscosity liquids or solids to aid removal from the reservoir. This type of surface would also improve grip on the balls. This type of surface could be used to deliver contents that has a particulate component e.g. Swarfega
4. A roughened surface wherein a high density of very small dimples 238 is provided (see FIG. 25). This could be used to aid grip between the roller and the user's hand, to receive and deliver the reservoir contents, and to act as an abrasive on the hand of the user. Thus, potentially aiding cleaning.

Materials

The dispenser 1 is manufactured from plastics materials. The alternatives or considerations are noted:
1. Polygiene—Polygiene employs ionic silver to inhibit the growth of micro-organisms. This can be added to the plastics material of the dispenser so as to make it more effective at killing bacteria.
2. Stainless steel—The rollers/balls may be made from stainless steel.
3. Soft touch—Soft Touch materials may be used on the body to make it more pleasing to use.
4. Transparent/Opaque/Translucent—The materials might be transparent or opaque/translucent to allow the user to see the product to be dispensed and internal workings of the dispenser.
5. Colour—Body, balls and liquid could have colours associated with them for identification of use, type, zoning etc.
6. Fabric—The body of the dispenser may be provided with a fabric coating. The back of the dispenser may have a fabric surface to prevent it rubbing the user.
7. Branding/Sponsorship—The dispenser may be provided with a space for receiving branding and sponsorship logos.

Clips

An important part of the design is the way in which it is held on or about the user. This is such as to encourage the user to clasp or otherwise use the dispenser. There are a number of ways in which a dispenser according to the present invention may be mounted:
1. Location. The device may be located anywhere on or about the user so to enable it to be accessed as desired. It can also be mounted to be a fixed location such as a kitchen or bathroom work surface, a cash register, a workstation etc.
2. Swinging clip. The clip is designed to allow the dispenser to move freely while still sitting with the rollers facing outwards. A walking motion of the user causes the device to bounce against the user and this results in a tendency for the user to claps the dispenser. This clasping action will assist in directing fluid to the rollers and dispensing an amount of liquid. The swinging clip is important in some design cases as it ensures that the device remains vertical wherever possible. This aids the mechanism of transfer.
3. Fixed stiff resilient clip, similar to that typically provide on a pen. This would be used to securely mount the device on a person or object so that it does not move or dangle if inclined. This clip type might be used on a dispenser intended for use in the home.
4. Straps. Elasticised straps with a tie or hook/loop fastener elements may be used to allow the device to be mounted around a wrist or other objects.
5. Hook and loop backing. The device may have a hook and loop or hook to hook type of backing to allow it to be attached to suitable hook and loop or hook to hook type mounting points e.g. at the side of a trolley, desk, monitor, car dashboard etc.
6. Lanyard. A lanyard may be used to attach the device around a users neck or hang the device from an object e.g. a door handle, a coat hook etc.
7. Magnet. A magnet may be incorporated into the back of the device to enable it to be attached to steel surfaces e.g. fridge doors, machinery etc.

Dispenser Configurations

Figure 36:
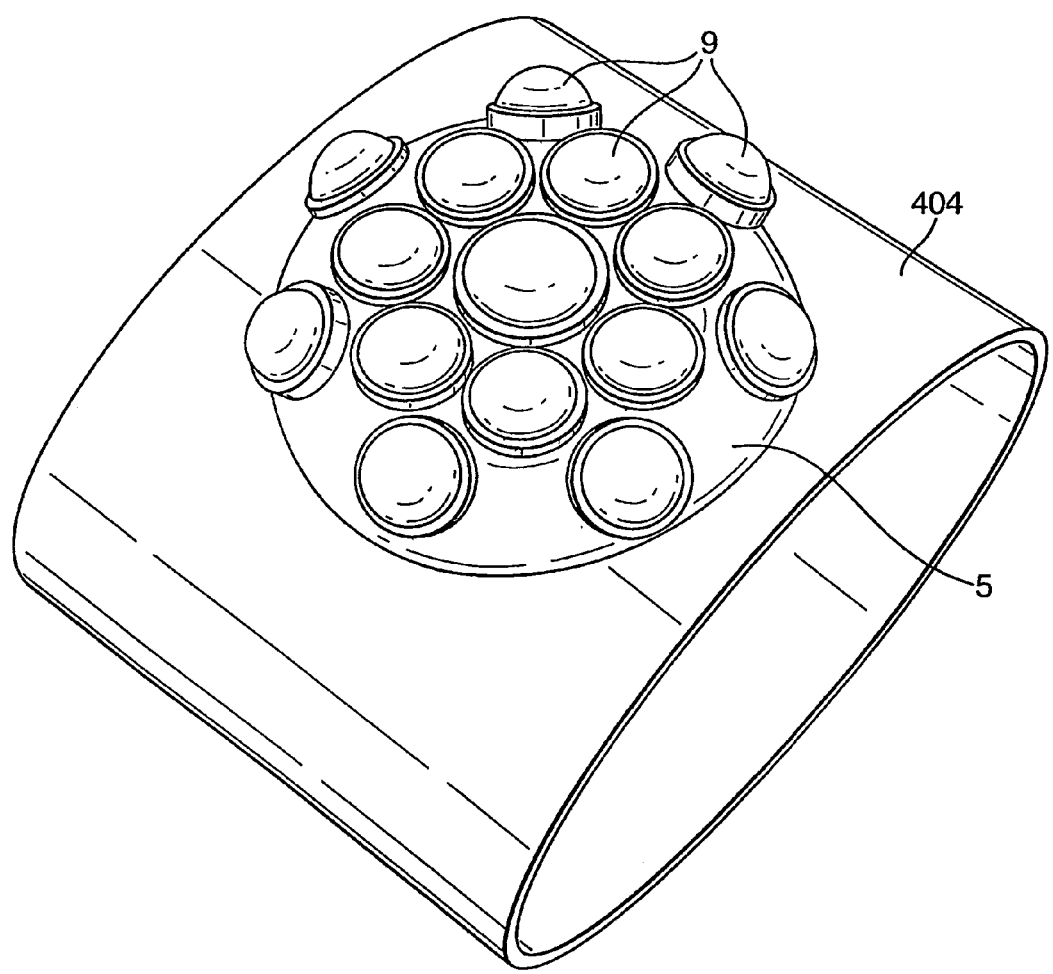
FIG. 36 is a perspective view of a further dispenser according to the present invention which is worn by a user about the wrist.
Figure 37:
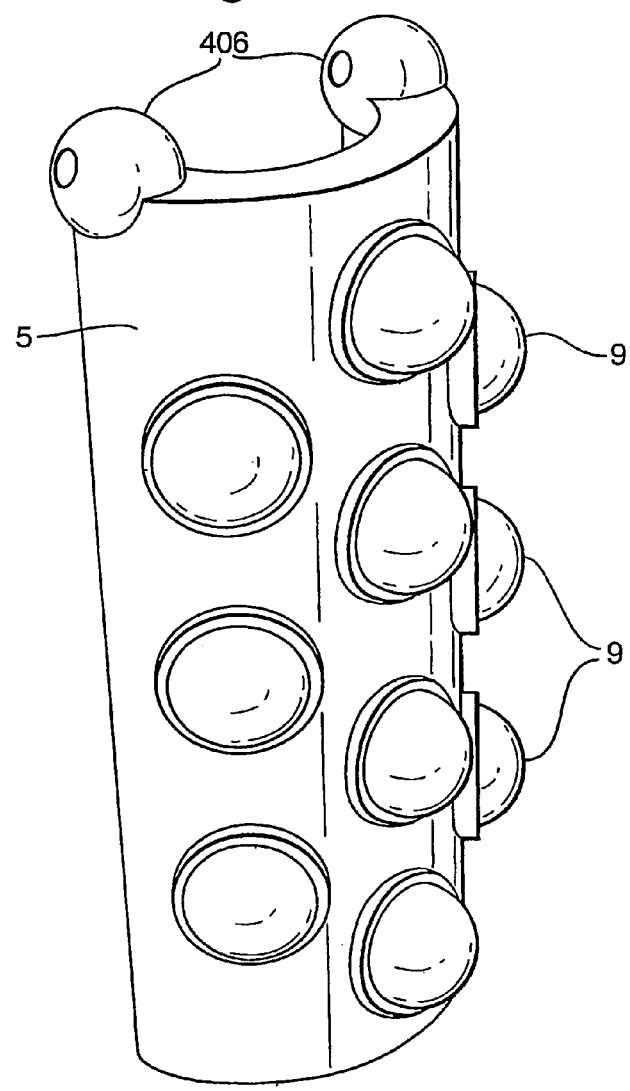
FIG. 37 is a perspective view of a yet further dispenser according to the present invention which is mounted to a lanyard.

There are also a number of product variants contemplated (in addition to the reservoir location) which include:
1. A device that can be worn on the wrist or arm. In such a device, the dispenser body may form a closed loop (i.e. a band) for locating about a user's wrist and the applicator is provided on the outer curved surface of the loop (see FIG. 36).
2. A double handed, or clasped, device that would be worn around the neck. This device may be the same as the first dispenser other than in that it is provided with rollers on the reverse side of the body as well as on the front side thereof. Alternatively, the rollers may be provided on the outer curved surface of a part-cylindrical body (see FIG. 37).

The present invention is not limited to the specific embodiment described above. Alternative arrangements and suitable materials will be apparent to a reader skilled in the art.

The invention claimed is:

1. A dispenser for dispensing a treatment product on to a hand, the dispenser comprising:
    an applicator, the applicator having a plurality of rollers for dispensing the treatment product,
    a treatment product storage reservoir in fluid communication with the applicator, the storage reservoir being deformable by a user during use to pressurize the storage reservoir, and
    a restraining means for restraining the dispenser to a support surface during use, such that when the hand is moved across the applicator, treatment product is applied to the hand.

2. The dispenser as claimed in claim 1, wherein, in use, movement of the hand across the applicator causes hand treatment product to be transported from the storage reservoir to the applicator.

3. The dispenser as claimed in claim 1, wherein the rollers are roller balls.

4. The dispenser as claimed in claim 1, wherein the restraining means is a clip suitable for clipping the dispenser to the user.

5. The dispenser as claimed in claim 1, wherein the dispenser is disposable.

6. The dispenser as claimed in claim 1, further comprising a cover, wherein the cover is arranged to cover the applicator.

7. The dispenser as claimed in claim 1, wherein the hand treatment product is colour coded.

8. The dispenser as claimed in claim 1, comprising means to indicate the level of hand treatment product in the reservoir.

9. The dispenser as claimed in claim 1, further comprising a scrubbing device.

10. The dispenser as claimed in claim 1, wherein the hand treatment product is a barrier cream or a moisturiser.

11. The dispenser as claimed in claim 1, wherein the hand treatment product is a cleanser.

12. The dispenser as claimed in claim 11, wherein the cleanser is a detergent.

13. The dispenser as claimed in claim 11, wherein the cleanser is a disinfectant.

14. The dispenser as claimed in claim 11, wherein the cleanser is an antiseptic.

15. The dispenser as claimed in claim 1, wherein the hand treatment product contains a pharmaceutically active agent.

16. The dispenser as claimed in claim 1, wherein the hand treatment product is a fluid.

17. The dispenser as claimed in claim 1, wherein the hand treatment product is an alcohol gel.

18. The dispenser as claimed in claim 1, wherein said restraining means is directly attached to said storage reservoir.

\* \* \* \* \*

UNITED STATES PATENT AND TRADEMARK OFFICE
CERTIFICATE OF CORRECTION

| | |
|---|---|
| PATENT NO. | : 8,714,853 B2 |
| APPLICATION NO. | : 12/308381 |
| DATED | : May 6, 2014 |
| INVENTOR(S) | : Adam F. R. Sutcliffe et al. |

It is certified that error appears in the above-identified patent and that said Letters Patent is hereby corrected as shown below:

In the Specification

Column 1, Line 14, "times a in" to read as --times in a--.

Column 1, Line 43, "to utilise another hand to apply it" to read as --to utilize another hand to apply it--.

Column 2, Line 30, "Preferably, the dispenser is colour coded" to read as --Preferably, the dispenser is color coded--.

Column 2, Line 35, "colour coded" to read as --color coded--.

Column 2, Line 65, "moisturiser" to read as --moisturizer--.

Column 3, Line 40, "Ideally, the surface of the or each roller" to read as --Ideally, the surface of each roller--.

Column 4, Lines 9-10, "arrangements for use as a alternative" to read as --arrangements for use as an alternative".

Column 5, Line 26, "dispenser 1," to read as --dispenser 1;--.

Column 5, Line 59, "resevoir" to read as --reservoir--.

Column 6, Lines 49-50, "This mechanism could be moulded" to read as --This mechanism could be molded--.

Column 6, Line 50, "on on" to read as --on--.

Signed and Sealed this
Third Day of March, 2015

Michelle K. Lee
*Deputy Director of the United States Patent and Trademark Office*

CERTIFICATE OF CORRECTION (continued)
U.S. Pat. No. 8,714,853 B2

Column 7, Line 39, "3. A coloured contact adhesive layer" to read as --3. A colored contact adhesive layer--.

Column 7, Line 42, "the colour of the adhesive" to read as --the color of the adhesive--.

Column 8, Line 4, "These uses are categorised" to read as --These uses are categorized--.

Column 8, Line 23, "they tend to use a double swipe, they" to read as --they tend to use a double swipe, and they--.

Column 8, Line 24, "hadn" to read as --hand--.

Column 8, Line 35, "the applicator be spaced" to read as --the applicator may be spaced--.

Column 10, Line 25, below "use." delete "5.".

Column 10, Line 61, "Swarfega" to read as --Swarfega.--.

Column 10, Line 66, "hand of the user. Thus potentially" to read as --hand of the user, thus potentially--.

Column 11, Line 15, "5. Colour – Body" to read as --5. Color – Body--.

Column 11, Line 38, "for the user to claps the dispenser" to read as --for the user to clasp the dispenser--.

Column 11, Line 57, "around a users neck or" to read as --around a user's neck or--.